US006894072B2

(12) United States Patent
Arasappan et al.

(10) Patent No.: US 6,894,072 B2
(45) Date of Patent: May 17, 2005

(54) COMPOUNDS AS NS3-SERINE PROTEASE INHIBITORS OF HEPATITIS C VIRUS

(75) Inventors: Ashok Arasappan, Bridgewater, NJ (US); Frank Bennett, Cranford, NJ (US); Stephane L. Bogen, Somerset, NJ (US); Kevin X. Chen, Edison, NJ (US); Edwin Jao, Warren, NJ (US); Yi-Tsung Liu, Morris Township, NJ (US); Raymond G. Lovey, West Caldwell, NJ (US); Vincent S. Madison, Mountain Lakes, NJ (US); Latha G. Nair, Edison, NJ (US); F. George Njoroge, Warren, NJ (US); Anil K. Saksena, Upper Montclair, NJ (US); Mousumi Sannigrahi, Summit, NJ (US); Srikanth Venkatraman, Woodbrige, NJ (US); Viyyoor M. Girijavallabhan, Parsippany, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/348,094

(22) Filed: Jan. 21, 2003

(65) Prior Publication Data

US 2003/0207861 A1 Nov. 6, 2003

Related U.S. Application Data

(60) Provisional application No. 60/350,931, filed on Jan. 23, 2002.

(51) Int. Cl.$^7$ .................... A61K 31/403; C07D 209/02; C07D 403/12

(52) U.S. Cl. ................... 514/422; 548/465; 548/469; 548/537; 548/950; 546/192; 544/359; 514/423

(58) Field of Search .................... 548/537, 465, 548/469, 950, 467; 514/422, 423, 414; 546/192; 544/359

(56) References Cited

U.S. PATENT DOCUMENTS 5,712,145 A 1/1998 Houghton et al.

FOREIGN PATENT DOCUMENTS

| EP | 381 216 | 8/1990 |
|---|---|---|
| WO | WO 89/04669 | 6/1989 |
| WO | WO 98/14181 | 4/1998 |
| WO | WO 98/17679 | 4/1998 |
| WO | WO 98/22496 | 5/1998 |
| WO | WO 99/07734 | 2/1999 |
| WO | WO 00/09543 | 2/2000 |
| WO | WO 00/09558 | 2/2000 |
| WO | WO 01/74768 | 10/2001 |
| WO | WO 02/08198 | 1/2002 |
| WO | WO 02/08244 | 1/2002 |
| WO | WO 02/08256 | 1/2002 |

OTHER PUBLICATIONS

Gumber, et al, Ann Intern Med. 1995, 123, 615–620.*
Leveque, et al, CMLS, 2002, 59, 909–919.*
Pizzi et al., "Molecular Model of the Specificity Pocket of the Hepatitis C. Virus Protease: Implications for the Substrate Recognition", *Proc. Natl. Acad. Sci.* (USA), 91: 888–892 (1994).
Failla et al., "Redesigning the Substrate Specificity of the Hepatitis C Virus NS3 Protease", *Folding & Design*, 1(1): 35–42 (1996).
Kolykhavlov et al., "Specificity of the Hepatitis C Virus NS3 Serine Protease: Effects of Substitutions at the 3/4A, 4A/4B, 4B/5A, and 5A/5B Cleavage Sites on Polyprotein Processing", *J. Virology*, 68(11): 7525–7533 (1994).
Komoda et al., "Substrate Requirements of Hepatitis C Virus Serine Proteinase for Intermolecular Polypeptide Cleavage in *Escherichia Coli*", *J. Virology*, 68(11): 7351–7357 (1994).
Landro et al., "Mechanistic Role of an NS4A Peptide Cofactor with the Truncated NS3 Protease of Hepatits C Virus: Elucidaiton of the NS4A Stimulatory Effect via Kinetic Analysis and Inhibitor Mapping", *Biochemistry*, 36: 9340–9348 (1997).
Ingallinella et al., "Potent Peptide Inhibitors of Human Hepatitis C Virus NS3 Protease Are Obtained by Optimizing the Cleavage Products" *Biochemistry*, 37: 8906–8914 (1998).
Llinàs–Brunet et al., "Studies on the C–Terminal of Hexapeptide Inhibitors of the Hepatitis C Virus Serine Protease", *Bioorg. Med. Chem. Lett.*, 8: 2719–2724 (1998).
Matin et al., "Design of Selective Eglin Inhibitors of HCV NS3 Proteinase", *Biochemistry*, 37: 11459–11468 (1998).
Dimasi et al., "Characterization of Engineered Hepatitis C Virus NS3 Protease Inhibitors Affinity Selected from Human Pancreatic Secretory Trypsin Inhibitor and Minibody Repertoires", *J. Virology*, 71(10): 7461–7469 (1997).
Martin et al., "Affinity Selection of a Camelized $V_H$ Domain Antibody Inhibitor of Hepatitis C Virius NS3 Protease", *Protein Engineering*, 10(5): 607–614 (1997).
Elzouki et al., "Serine Protease Inhibitors in Patients with Chronic Viral Hepatitis", *J. Hepatology*, 27: 42–48 (1997).
BioWorld Today, 9(217): 4 (Nov. 10, 1998).
Berenguer et al., "Hepatitis B and C Viruses: Molecular Identification and Targeted Antiviral Therapies", *Proc. Assoc. Amer. Physicians*, 110(2): 98–112 (1998).
Hoofnagle et al., "The Treatment of Chronic Viral Hepatitis", *N. Engl. J. Med.*, 336(5): 347–356 (1997).

(Continued)

Primary Examiner—Golam M M Shameem
(74) Attorney, Agent, or Firm—Palaiyur S. Kalyanaraman

(57) ABSTRACT

The present invention discloses novel compounds which have HCV protease inhibitory activity as well as methods for preparing such compounds. In another embodiment, the invention discloses pharmaceutical compositions comprising such compounds as well as methods of using them to treat disorders associated with the HCV protease.

25 Claims, No Drawings-

OTHER PUBLICATIONS

R. Zhang et al., "Design Synthesis and Evaluation of Poly–L–Proline Type–II Peptide Mimics Based on the 3–Azabicyclo[3.1.0]hexane System", *J. Org. Chem.*, 64: 330–331 (1999).

D. L. Sali et al., "Serine Protease of Hepatitis C Virus Expressed in Insect Cells as the NS3/4A Complex", *Biochemistry*, 37: 3392–3401 (1998).

K. Barlos et al., "2–Chlorothityl Chloride Resin . . . Studies on anchoring of Fmoc–amino acids and peptide cleavage", Int. J. Pept. Protein Res., 37: 513–520 (1991).

K. Holmberg et al., "Ester Synthesis with Dicyclohexylcarbodiimide Improved by Acid Catalysts", Acta. Chem Scand., B33: 410–412 (1979).

A. Marchetti et al., "Synthesis of Two Novel Cyclic Biphenyl Ether Analogs of an Inhibitor of HCV NS3 Protease", *Synlett*, S1: 1000–1002 (1999).

W Han et al., "α–Ketoamides, α–Ketoesters and α–Diketones as HCV NS3 Protease Inhibitors", *Bioorganic & Medicinal Chem. Lett.*, 10: 711–713 (2000).

S. Agrawal et al., "Development and Characterization of Hepatitis C Virus Serine Protease Cell–based Trans–Cleavage Assay", Hepatology Supplement to vol. 30 (No. 4, Part 2, Oct. 1999), Abstract No. 615 (Proceedings of AASLD 50th Annual Meeting, Dallas, Texas, Nov. 5–9, 1999.

D. L. Hughs, "The Mitsunobu Reaction", *Organic Reactions*, 42: 335–395 (1992).

R. F. Heck, "Palladium–Catalyzed Vinylation of Organic Halides", *Organic Reactions*, 27: 345–391 (1989).

* cited by examiner

US 6,894,072 B2

COMPOUNDS AS NS3-SERINE PROTEASE INHIBITORS OF HEPATITIS C VIRUS

This patent application claims priority from U.S. provisional patent application Ser. No. 60/350,931, filed Jan. 23, 2002.

FIELD OF INVENTION

The present invention relates to novel hepatitis C virus ("HCV") protease inhibitors, pharmaceutical compositions containing one or more such inhibitors, methods of preparing such inhibitors and methods of using such inhibitors to treat hepatitis C and related disorders. This invention specifically discloses novel peptide compounds as inhibitors of the HCV NS3/NS4a serine protease. The invention disclosed in this application is related to that in patent application Ser. No. 10/052,386, filed Jan. 18, 2002.

BACKGROUND OF THE INVENTION

Hepatitis C virus (HCV) is a (+)-sense single-stranded RNA virus that has been implicated as the major causative agent in non-A, non-B hepatitis (NANBH), particularly in blood-associated NANBH (BB-NANBH)(see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliary cirrhosis.

Recently, an HCV protease necessary for polypeptide processing and viral replication has been identified, cloned and expressed; (see, e.g., U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (i.e., trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, e.g., Pizzi et al. (1994) *Proc. Natl. Acad. Sci* (*USA*) 91:888–892, Failla et al. (1996) *Folding & Design* 1:35–42. The NS3/NS4a cleavage site is also more tolerant of mutagenesis than the other sites. See, e.g., Kollykhalov et al. (1994) *J. Virol.* 68:7525–7533. It has also been found that acidic residues in the region upstream of the cleavage site are required for efficient cleavage. See, e.g., Komoda et al. (1994) *J. Virol.* 68:7351–7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) *Biochem.* 36:9340–9348, Ingallinella et al. (1998) *Biochem.* 37:8906–8914, Llinàs-Brunet et al. (1998) *Bioorg. Med. Chem. Lett.* 8:1713–1718), inhibitors based on the 70-amino acid polypeptide eglin c (Martin et al. (1998) *Biochem.* 37:11459–11468, inhibitors affinity selected from human pancreatic secretory trypsin inhibitor (hPSTI-C3) and minibody repertoires (MBip) (Dimasi et al. (1997) *J. Virol.* 71:7461–7469), $CV_HE2$ (a "camelized" variable domain antibody fragment) (Martin et al.(1997) *Protein Eng.* 10:607–614), and α1-antichymotrypsin (ACT) (Elzouki et al.) (1997) *J. Hepat.* 27:42–28). A ribozyme designed to selectively destroy hepatitis C virus RNA has recently been disclosed (see, *BioWorld Today* 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (F. Hoffmann-La Roche AG); and WO 99/07734, published Feb. 18, 1999 (Boehringer Ingelheim Canada Ltd.).

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10–30%, whereas those with localized unresectable hepatocellular carcinoma have a five-year survival rate of less than 1%.

Reference is made to A. Marchetti et al, *Synlett*, S1, 1000–1002 (1999) describing the synthesis of bicylic analogs of an inhibitor of HCV NS3 protease. A compound disclosed therein has the formula:

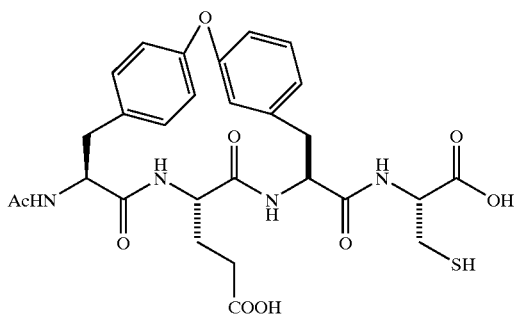

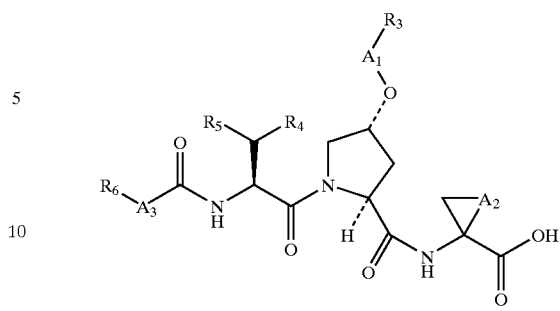

where the various elements are defined therein. An illustrative compound of that series is:

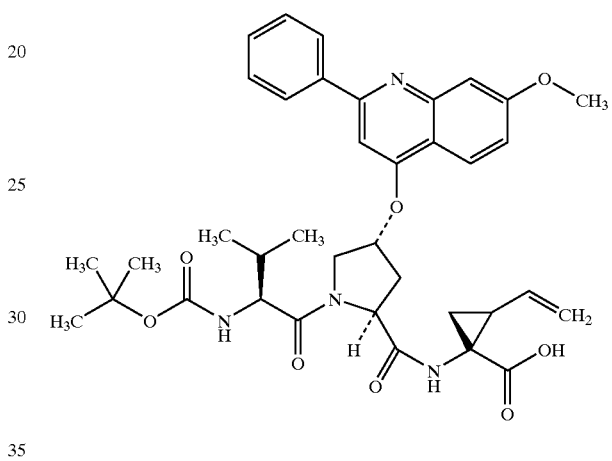

Reference is also made to W. Han et al, *Bioorganic & Medicinal Chem. Lett*, (2000) 10, 711–713, which describes the preparation of certain α-ketoamides, α-ketoesters and α-diketones containing allyl and ethyl functionalities.

Reference is also made to WO 00/09558 (Assignee: Boehringer Ingelheim Limited; Published Feb. 24, 2000) which discloses peptide derivatives of the formula:

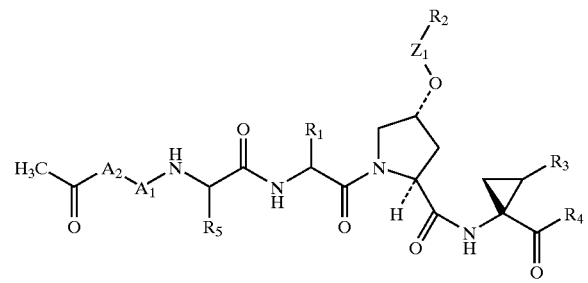

Current therapies for hepatitis C include interferon-α (TNF$_\alpha$) and combination therapy with ribavirin and interferon. See, e.g., Beremguer et al. (1998) *Proc. Assoc. Am. Physicians* 110(2):98–112. These therapies suffer from a low sustained response rate and frequent side effects. See, e.g., Hoofnagle et al. (1997) *N. Engl. J. Med.* 336:347. Currently, no vaccine is available for HCV infection.

Reference is further made to WO 01/74768 (Assignee: Vertex Pharmaceuticals Inc) published Oct. 11, 2001, which discloses certain compounds of the following general formula (R is defined therein) as NS3-serine protease inhibitors of Hepatitis C virus:

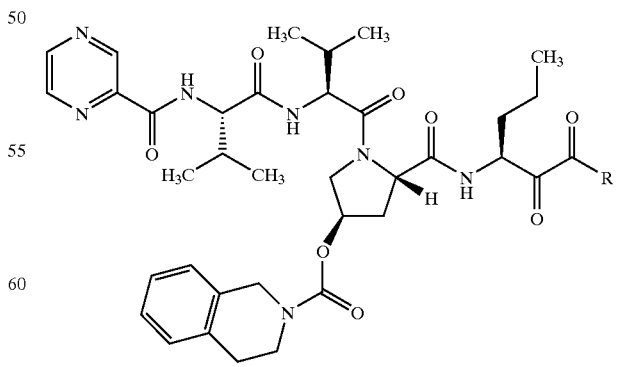

where the various elements are defined therein. An illustrative compound of that series is:

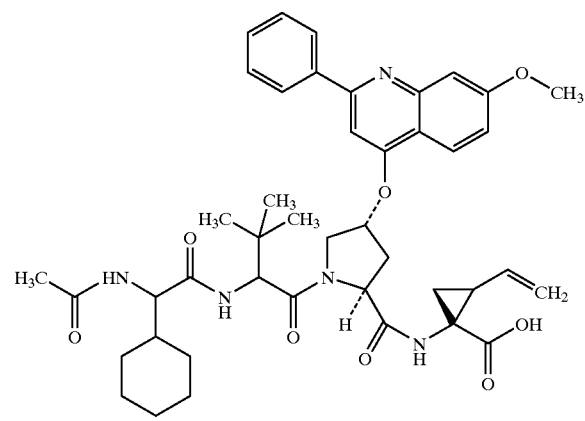

Reference is also made to WO 00/09543 (Assignee: Boehringer Ingelheim Limited; Published Feb. 24, 2000) which discloses peptide derivatives of the formula:

A specific compound disclosed in the aforementioned WO 01/74768 has the following formula:

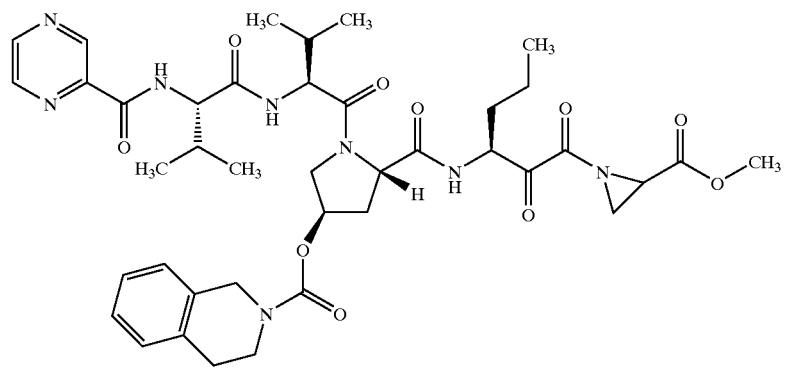

Pending U.S. patent applications Ser. No. 09/825,399 filed Apr. 3, 2001 (PCT Publication No. WO 01/77113 published Oct. 18, 2001); Ser. No. 09/836,636 filed Apr. 17, 2001(PCT Publication No. WO 01/81325 published Nov. 1, 2001); Ser. No. 09/909,077 filed Jul. 19, 2001(PCT Publication No. WO 02/08198 published Jan. 31, 2002); Ser. No. 909,062 filed Jul. 19, 2001(PCT Publication No. WO 02/08256 published Jan. 31, 2002); Ser. No. 909,012 filed Jul. 19, 2001(PCT Publication No. WO 02/08187 published Jan. 31, 2002); Ser. No. 908,955 filed Jul. 19, 2001 (PCT Publication No. WO 02/08244 published Jan. 31, 2002); Ser. No. 10/013,071 filed Dec. 10, 2001 (PCT Publication No. WO 02/48172 published Jun. 20, 2002); Ser. No. 09/909,164 filed Jul. 19, 2001 (PCT Publication No. WO 02/08251 published Jan. 31, 2002); and the afore-mentioned patent application Ser. No. 10/052,386, filed Jan. 18, 2002 disclose various types of peptides and/or other compounds as NS-3 serine protease inhibitors of hepatitis C virus. The disclosures of those applications are incorporated herein by reference thereto.

There is a need for new treatments and therapies for HCV infection. It is, therefore, an object of this invention to provide compounds useful in the treatment or prevention or amelioration of one or more symptoms of hepatitis C.

It is a further object herein to provide methods of treatment or prevention or amelioration of one or more symptoms of hepatitis C.

A still further object of the present invention is to provide methods for modulating the activity of serine proteases, particularly the HCV NS3/NS4a serine protease, using the compounds provided herein.

Another object herein is to provide methods of modulating the processing of the HCV polypeptide using the compounds provided herein.

SUMMARY OF THE INVENTION

In its many embodiments, the present invention provides a novel class of inhibitors of the HCV protease, pharmaceutical compositions containing one or more of the compounds, methods of preparing pharmaceutical formulations comprising one or more such compounds, and methods of treatment, prevention or amelioration or one or more of the symptoms of hepatitis C. Also provided are methods of modulating the interaction of an HCV polypeptide with HCV protease. Among the compounds provided herein, compounds that inhibit HCV NS3/NS4a serine protease activity are preferred. The present application discloses a compound, or enantiomers, stereoisomers, rotamers, tautomers, racemates or prodrug of said compound, or pharmaceutically acceptable salts or solvates of said compound, or pharmaceutically acceptable salts or solvates of said prodrug, said compound having the general structure shown in Formula I:

Formula I

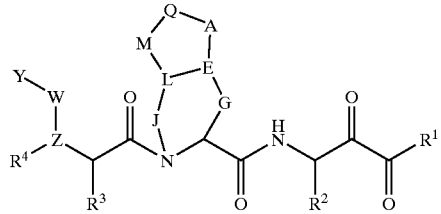

wherein:

Y is selected from the group consisting of the following moieties: alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino and heterocycloalkylamino, with the proviso that Y maybe optionally substituted with $X^{11}$ or $X^{12}$;

$X^{11}$ is alkyl, alkenyl, alkynyl, cycloalkyl, cycloalkylalkyl, heterocyclyl, heterocyclylalkyl, aryl, alkylaryl, arylalkyl, heteroaryl, alkylheteroaryl, or heteroarylalkyl, with the proviso that $X^{11}$ may be additionally optionally substituted with $X^{12}$;

$X^{12}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxyl, carbalkoxy (the term "carbalkoxy" means ester), carboxamido (the term "carboxamido" means amide), alkoxycarbonylamino, alkoxycarbonyloxy, alkylureido, arylureido, halogen, cyano, or nitro, with the proviso that said alkyl, alkoxy, and aryl may be additionally optionally substituted with moieties independently selected from $X^{12}$;

$R^1$ is selected from the following structures:

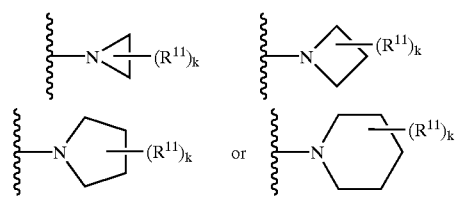

wherein k is a number from 0 to 5, which can be the same or different, $R^{11}$ denotes optional substituents on the ring, with each of said substituents being independently selected from the group consisting of H, alkyl, alkenyl, alkynyl, aryl, cycloalkyl, alkyl-aryl, heteroalkyl, heteroaryl, aryl-heteroaryl, alkyl-heteroaryl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino, heterocycloalkylamino, hydroxy, thio, alkylthio, arylthio, amino, alkylsulfonyl, arylsulfonyl, alkylsulfonamido, arylsulfonamido, carboxyl, carbalkoxy, carboxamido, alkoxycarbonylamino, alkoxycarbonyloxy, alkylureido, arylureido, halogen, cyano, and nitro, with the proviso that $R^{11}$ (when $R^{11} \neq H$) maybe additionally optionally substituted with $X^{11}$ or $X^{12}$;

Z is selected from O, N, CH or CR;

W may be present or absent, and if W is present, W is selected from C=O, C=S, C(=N—CN), or $SO_2$;

Q may be present or absent, and when Q is present, Q is CH, N, P, $(CH_2)_p$, $(CHR)_p$, $(CRR')_p$, O, NR, S, or $SO_2$; and when Q is absent, M may be present or absent; when Q and M are absent, A is directly linked to L;

A is O, $CH_2$, $(CHR)_p$, $(CHR—CHR')_p$, $(CRR')_p$, NR, S, $SO_2$ or a bond;

E is CH, N, CR, or a double bond towards A, L or G;

G may be present or absent, and when G is present, G is $(CH_2)_p$, $(CHR)_p$, or $(CRR')_p$; and when G is absent, J is present and E is directly connected to the carbon atom in Formula I as G is linked to;

J maybe present or absent, and when J is present, J is $(CH_2)_p$, $(CHR)_p$, or $(CRR')_p$, $SO_2$, NH, NR or O; and when J is absent,: G is present and E is directly linked to N shown in Formula I as linked to J;

L may be present or absent, and when L is present, L is CH, CR, O, S or NR; and when L is absent, then M may be present or absent; and if M is present with L being absent, then M is directly and independently linked to E, and J is directly and independently linked to E;

M may be present or absent, and when M is present, M is O, NR, S, $SO_2$, $(CH_2)_p$, $(CHR)_p(CHR—CHR')_p$, or $(CRR')_p$;

p is a number from 0 to 6; and

R, R', $R^2$, $R^3$ and $R^4$ are independently selected from the group consisting of H; $C_1$–$C_{10}$ alkyl; $C_2$–$C_{10}$ alkenyl; $C_3$–$C_8$ cycloalkyl; $C_3$–$C_8$ heterocycloalkyl, alkoxy, aryloxy, alkylthio, arylthio, amino, amido, ester, carboxylic acid, carbamate, urea, ketone, aldehyde, cyano, nitro, halogen;

(cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms;

aryl; heteroaryl; alkyl-aryl; and alkyl-heteroaryl;

wherein any of the above-said alkyl, heteroalkyl, alkenyl, heteroalkenyl, aryl, heteroaryl, cycloalkyl and heterocycloalkyl moieties may be independently and optionally substituted, with said term "substituted" referring to optional substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamido, sulfoxide, sulfone, sulfonyl urea, hydrazide, and hydroxamate;

further wherein said unit N-C-G-E-L-J-N represents a five-membered or six-membered cyclic ring structure with the proviso that when said unit N-C-G-E-L-J-N represents a five-membered cyclic ring structure, or when the bicyclic ring structure in Formula I comprising N, C, G, E, L, J, N, A, Q, and M represents a five-membered cyclic ring structure, then said five-membered cyclic ring structure lacks a carbonyl group as part of the cyclic ring.

The compounds of Formula I can be useful as inhibitors of HCV protease and can be useful in the treatment and prevention of diseases associated with such protease.

DESCRIPTION OF THE INVENTION

In one embodiment, the present invention discloses compounds of Formula I as inhibitors of HCV protease, especially the HCV NS3/NS4 serine protease, or a pharmaceutically acceptable derivative thereof, where the various definitions are given above.

Among the above-stated definitions for the various moieties of Formula I, the preferred groups for the various moieties are as follows:

Preferred definitions for $R^1$ are:

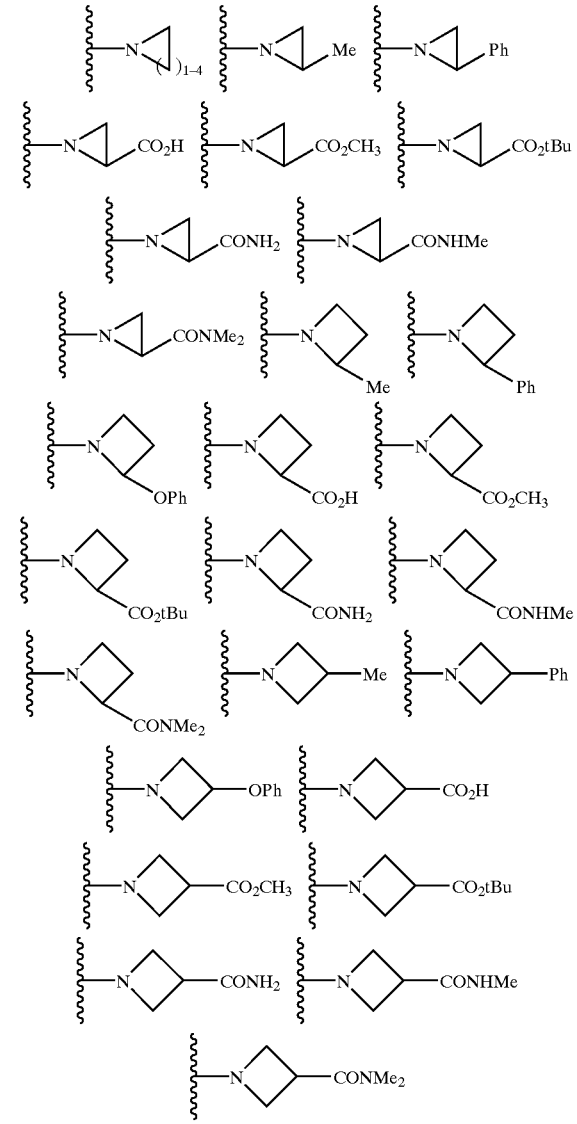

Preferred moieties for $R^2$ are:
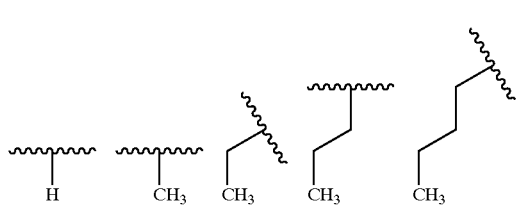
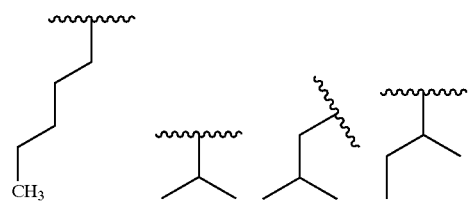
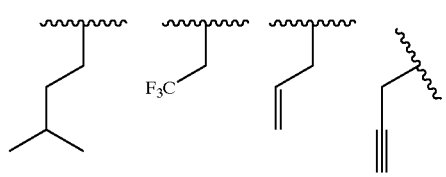
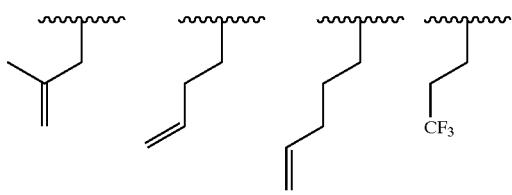
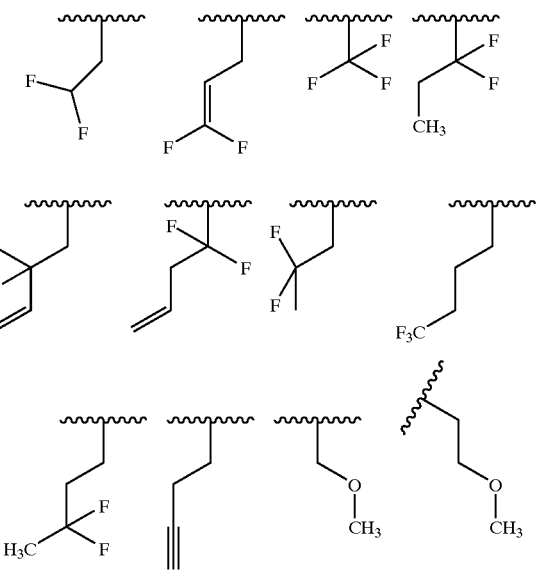
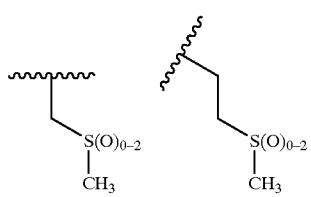
Additional preferred moieties for $R^2$ include the following:
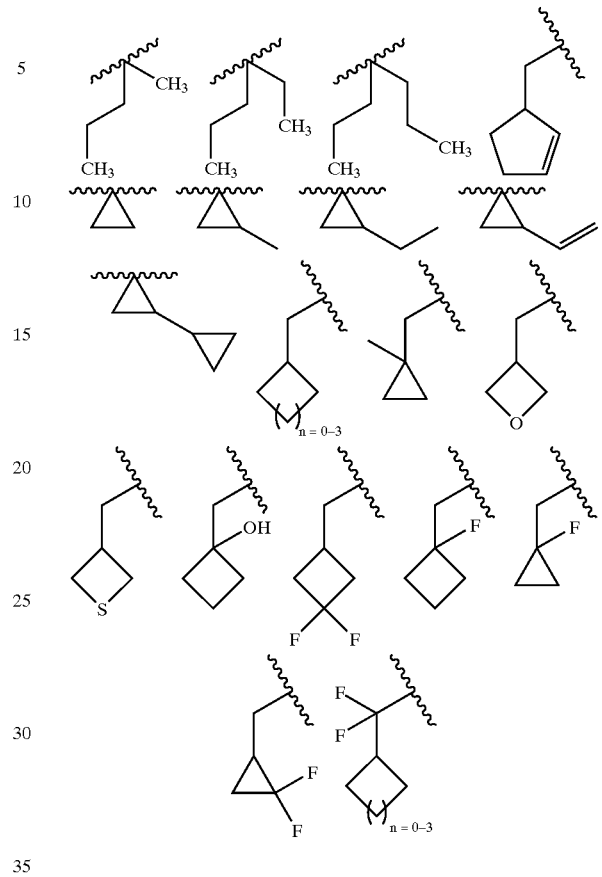
Preferred moieties for $R^3$ are:
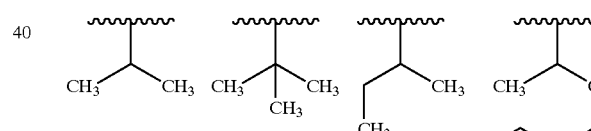
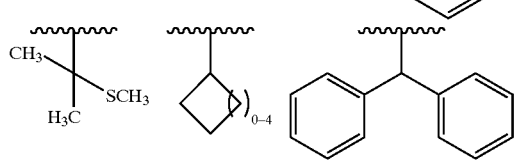
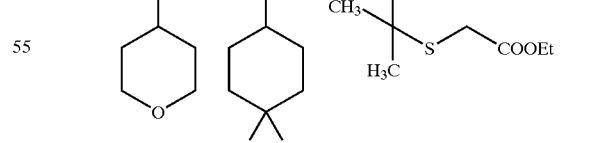
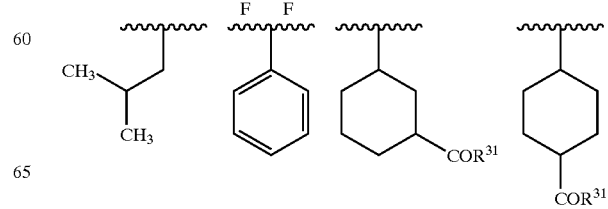

-continued
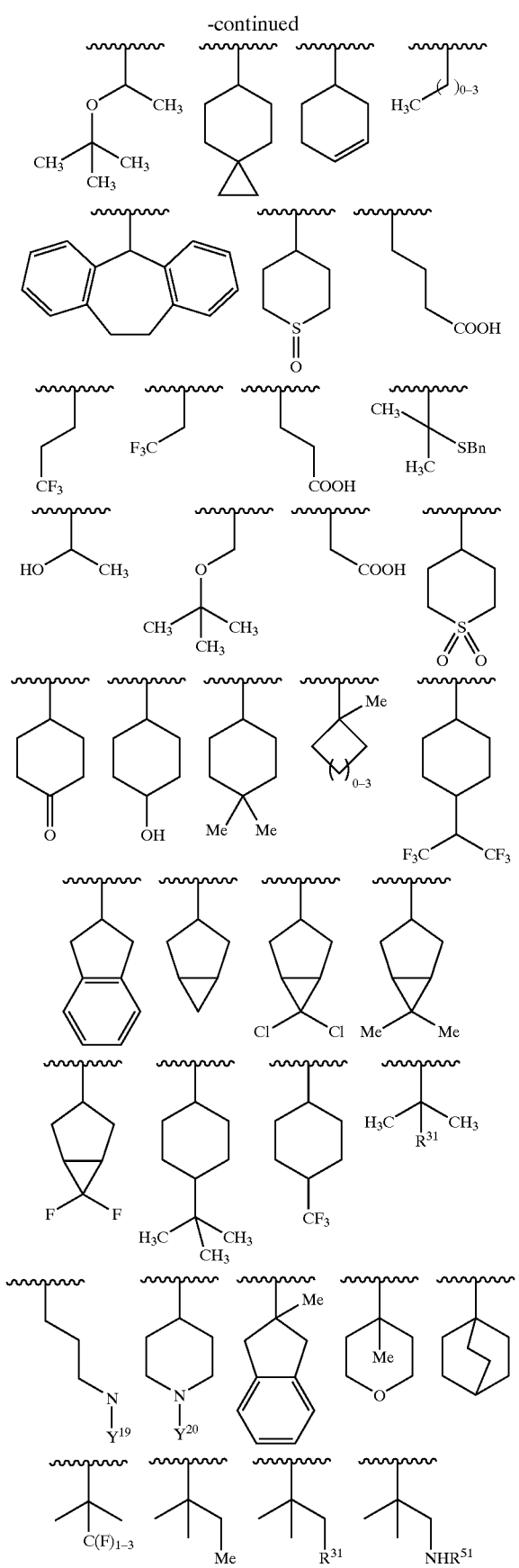
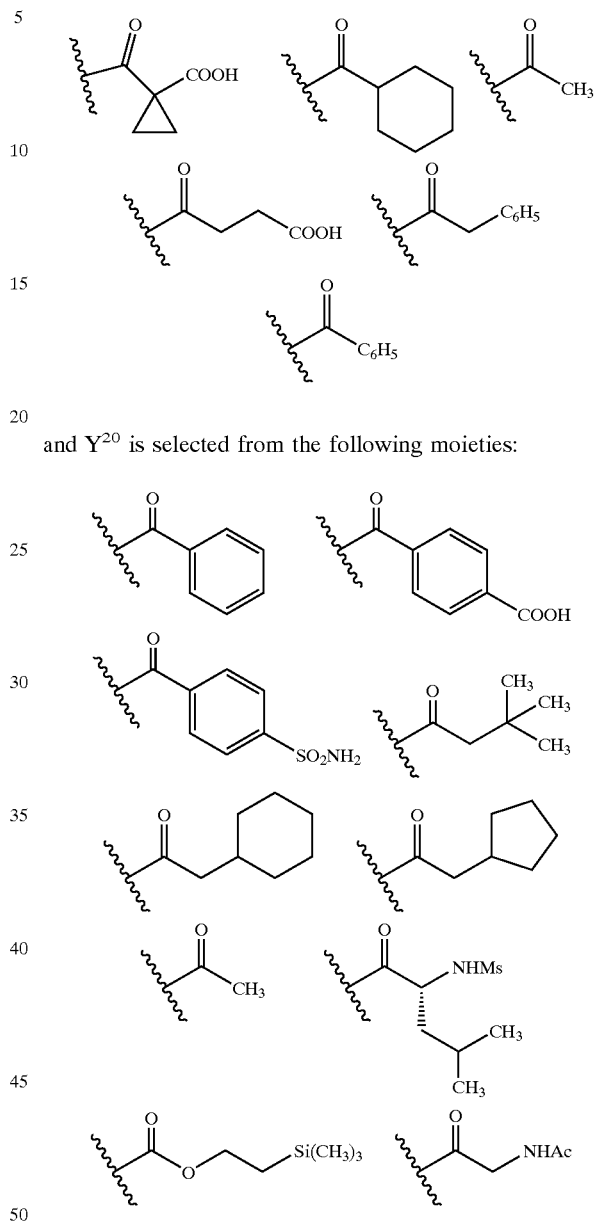
wherein $R^{31}$=OH or O-alkyl;
$R^{51}$=H, COCH$_3$, COOtBu or CONHtBu;
$Y^{19}$ is selected from the following moieties:
and $Y^{20}$ is selected from the following moieties:
Most preferred moieties for $R^3$ are:
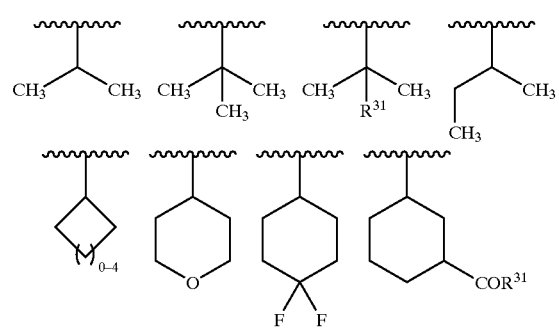

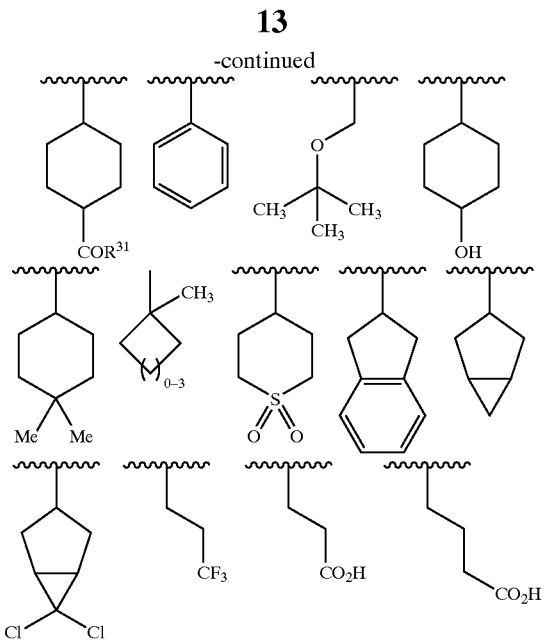
Some other preferred moieties are:
for Z it is N, for $R^4$ it is H, and for W it is C=O.
Additionally, the moiety Z-C—$R^3$ in Formula I, with $R^4$ being absent, may be represented by the following structures:
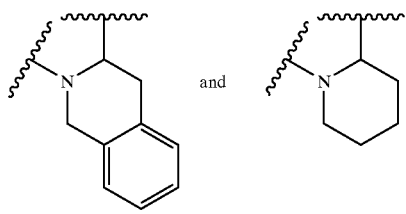
Preferred moieties for Y are:
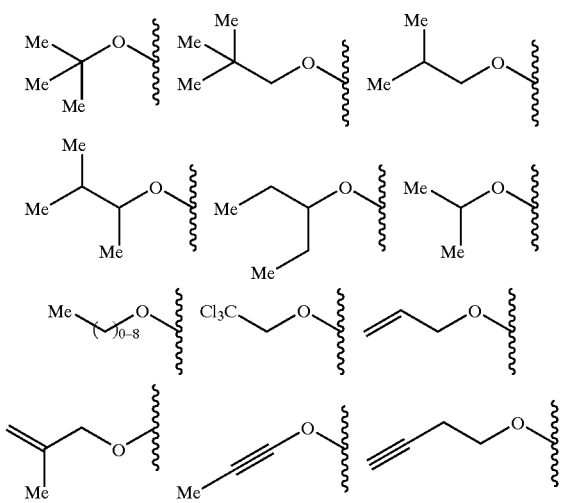
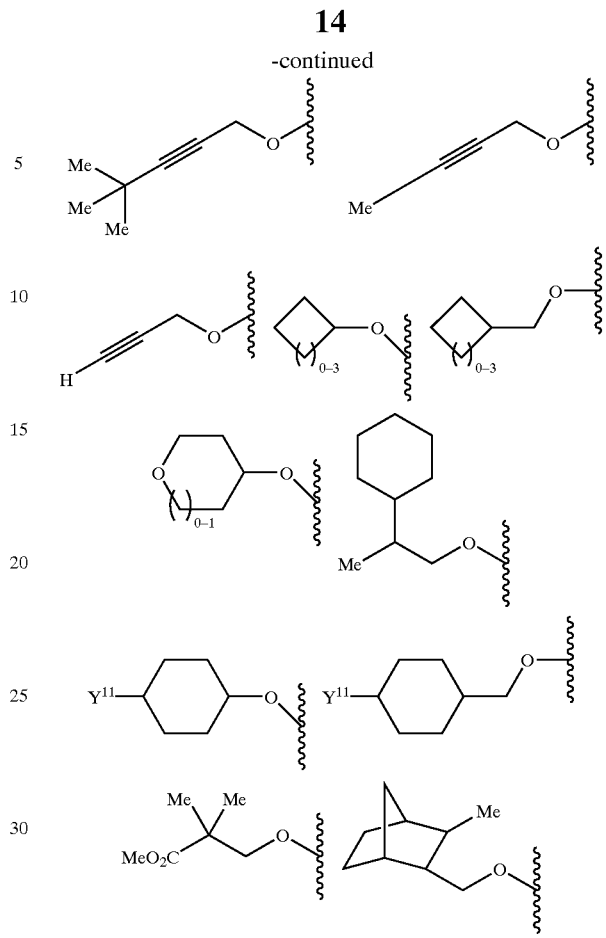
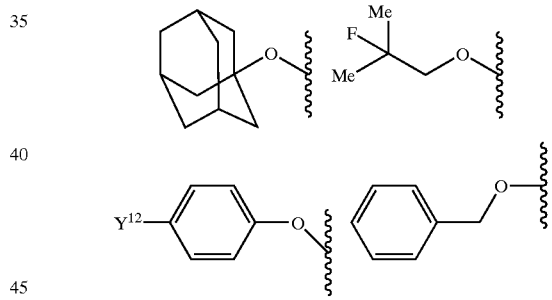
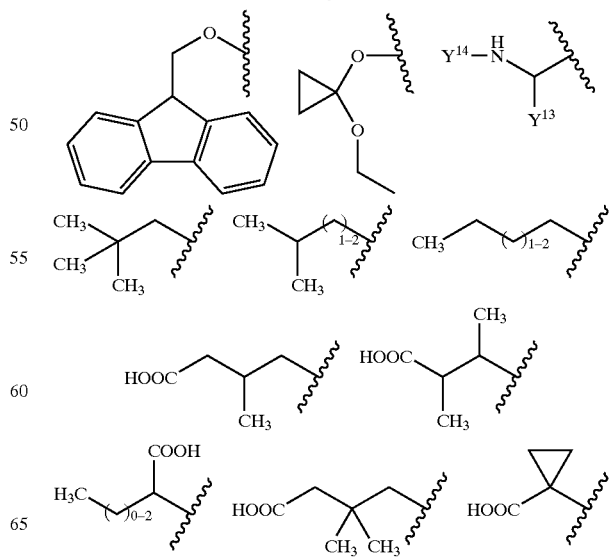

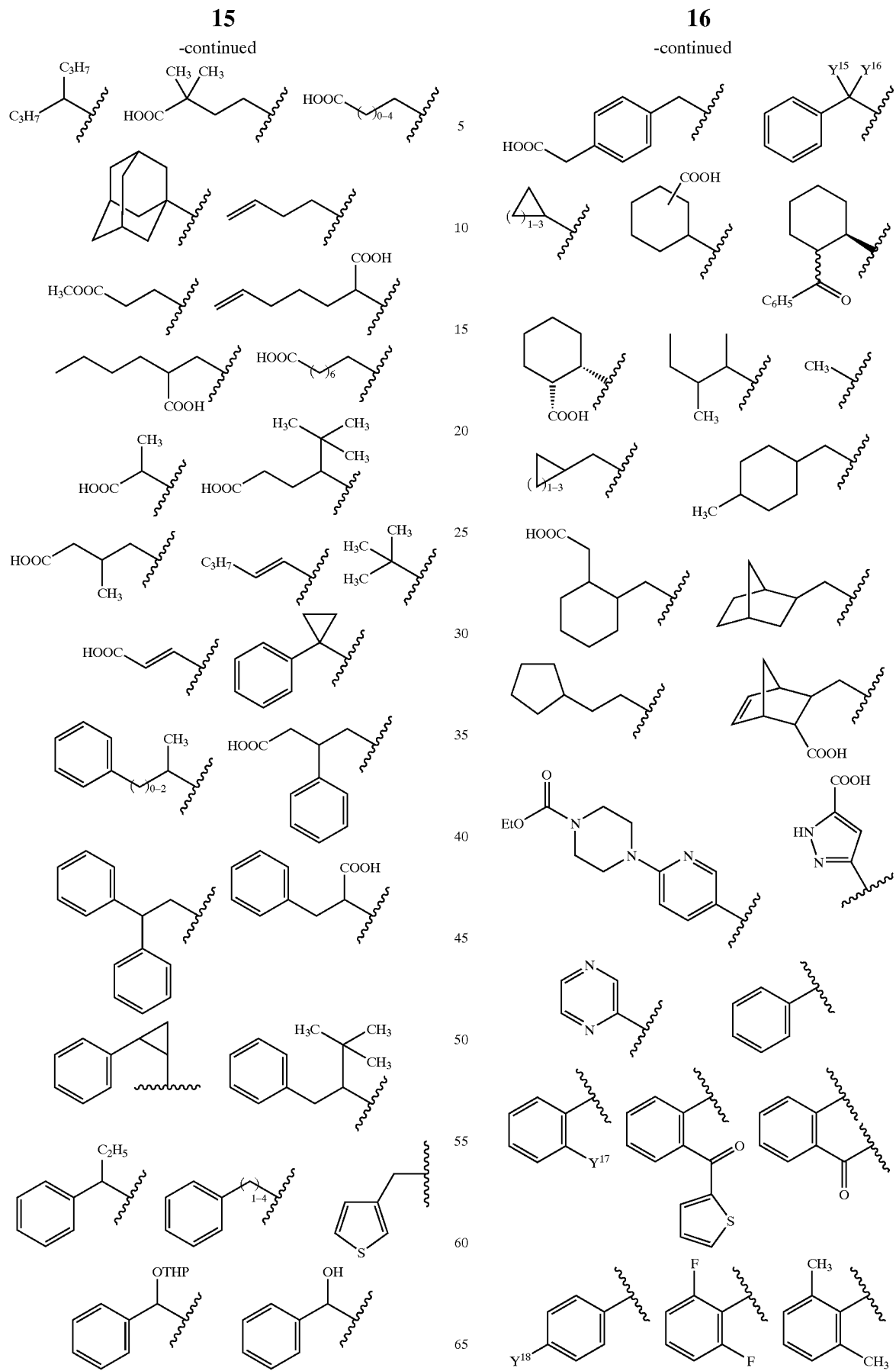

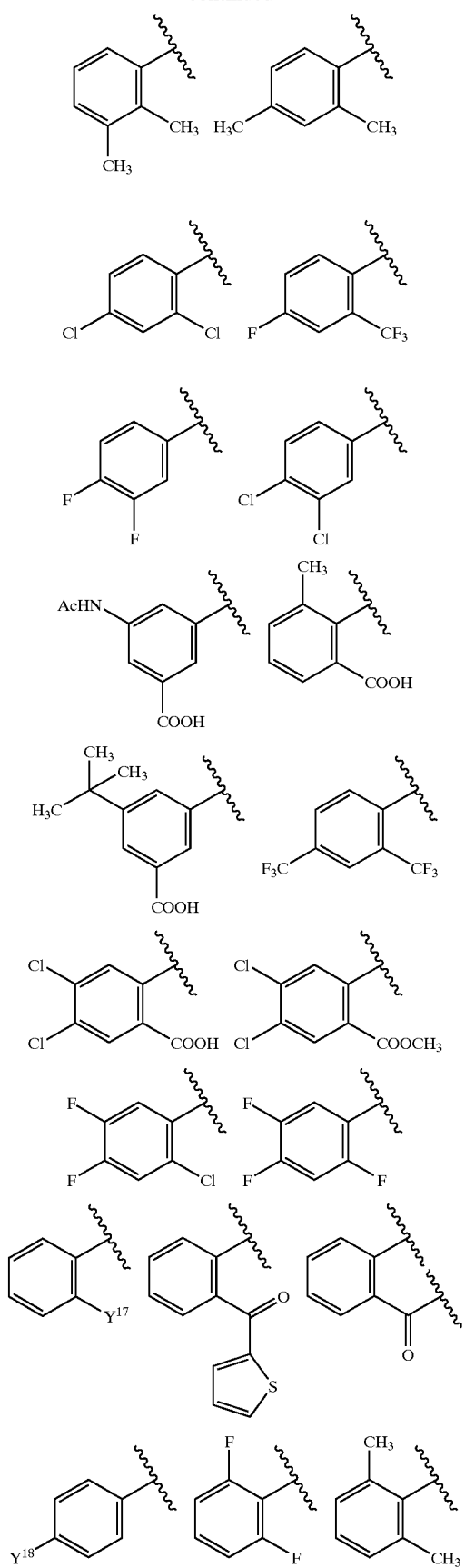
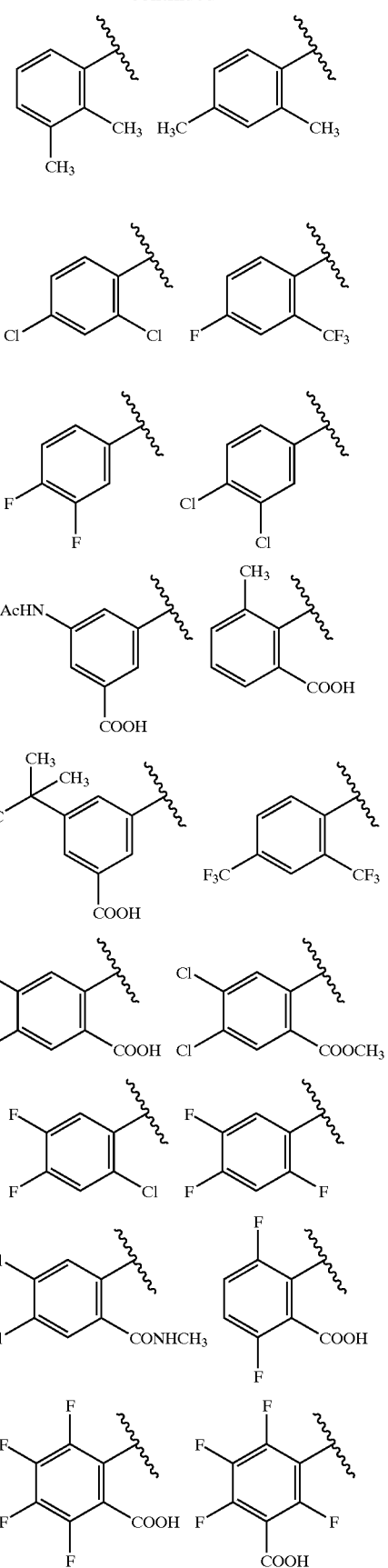

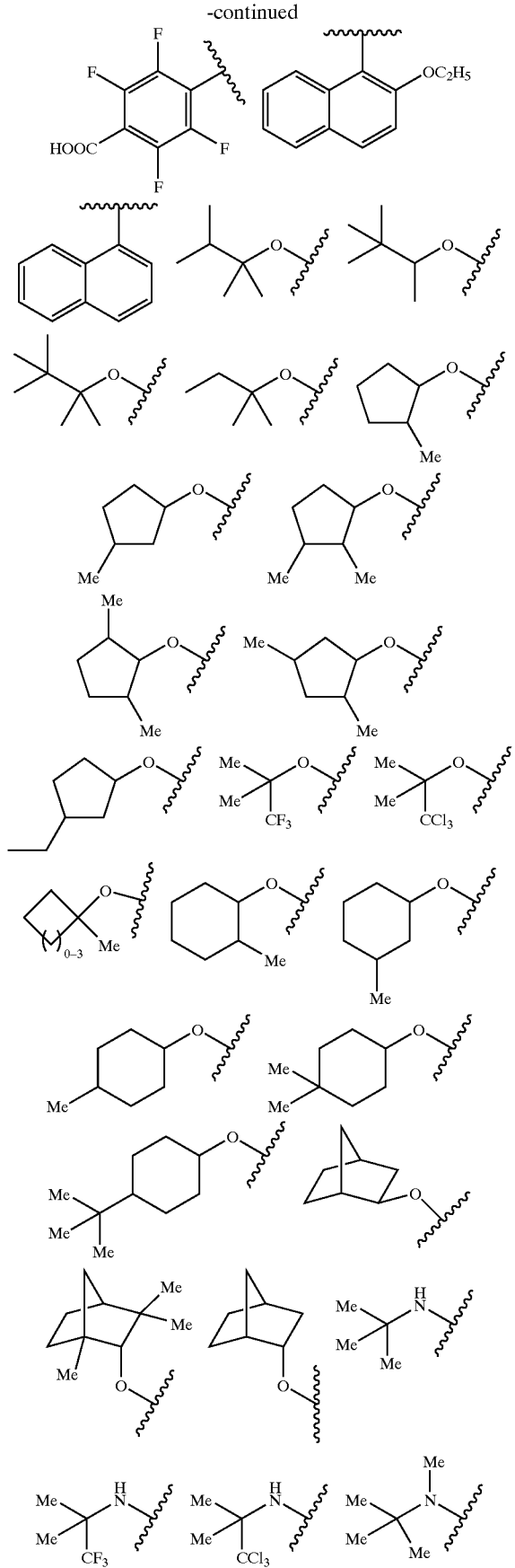
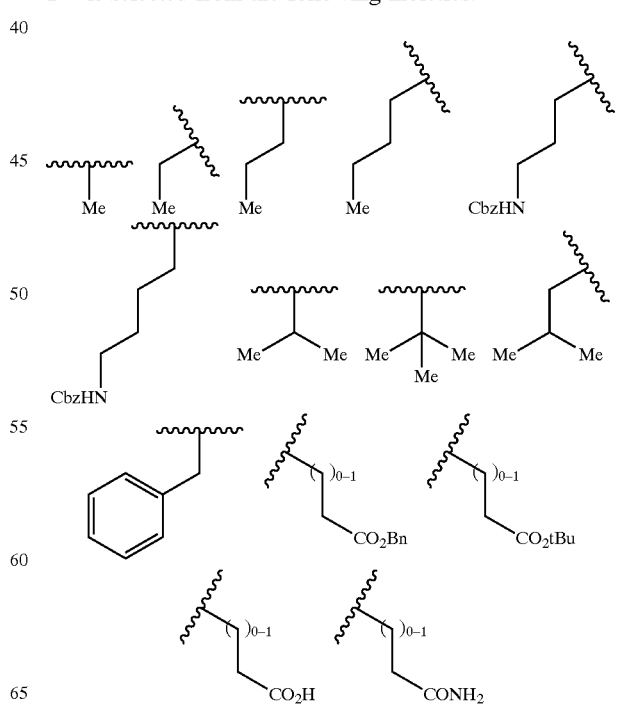
wherein:
$Y^{11}$ is selected from H, COOH, COOEt, OMe, Ph, OPh, NHMe, NHAc, NHPh, CH(Me)$_2$, 1-triazolyl, 1-imidazolyl, and NHCH$_2$COOH;
$Y^{12}$ is selected from H, COOH, COOMe, OMe, F, Cl, or Br;
$Y^{13}$ is selected from the following moieties:

$Y^{14}$ is selected from the following moieties:
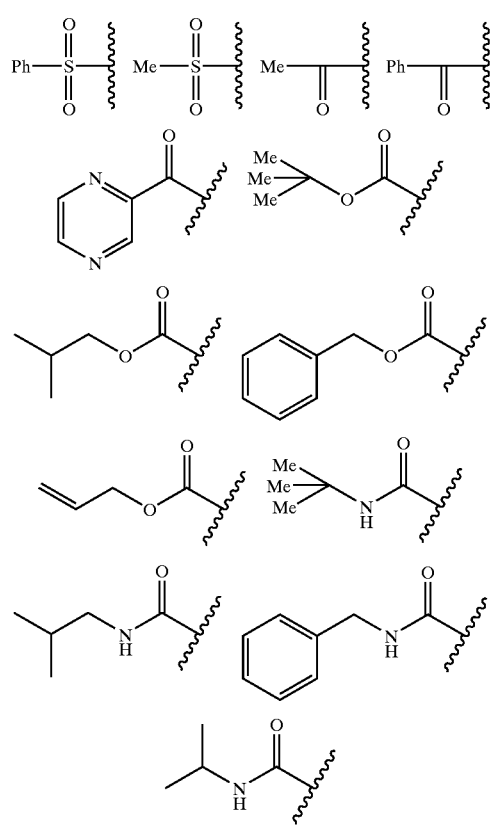
$Y^{15}$ and $Y^{16}$ are independently selected from alkyl, aryl, heteroalkyl, and heteroaryl;
$Y^{17}$ is $CF_3$, $NO_2$, $CONH_2$, $OH$, $COOCH_3$, $OCH_3$, $OC_6H_5$, $C_6H_5$, $COC_6H_5$, $NH_2$, or $COOH$; and
$Y^{18}$ is $COOCH_3$, $NO_2$, $N(CH_3)_2$, $F$, $OCH_3$, $CH_2COOH$, $COOH$, $SO_2NH_2$, or $NHCOCH_3$.
Y may be more preferably represented by:
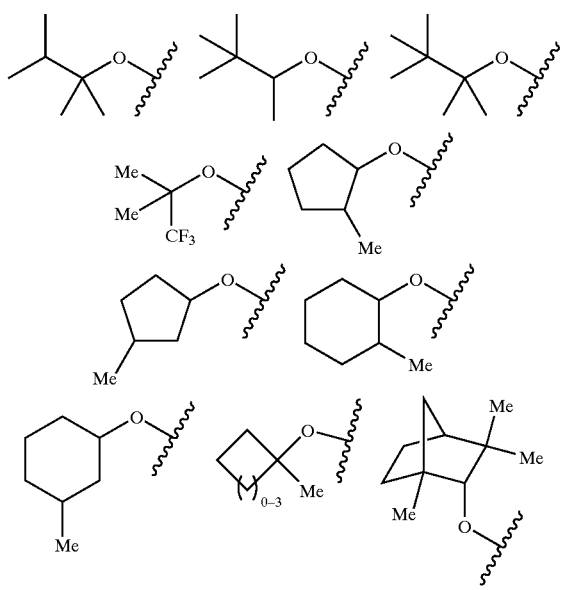
-continued
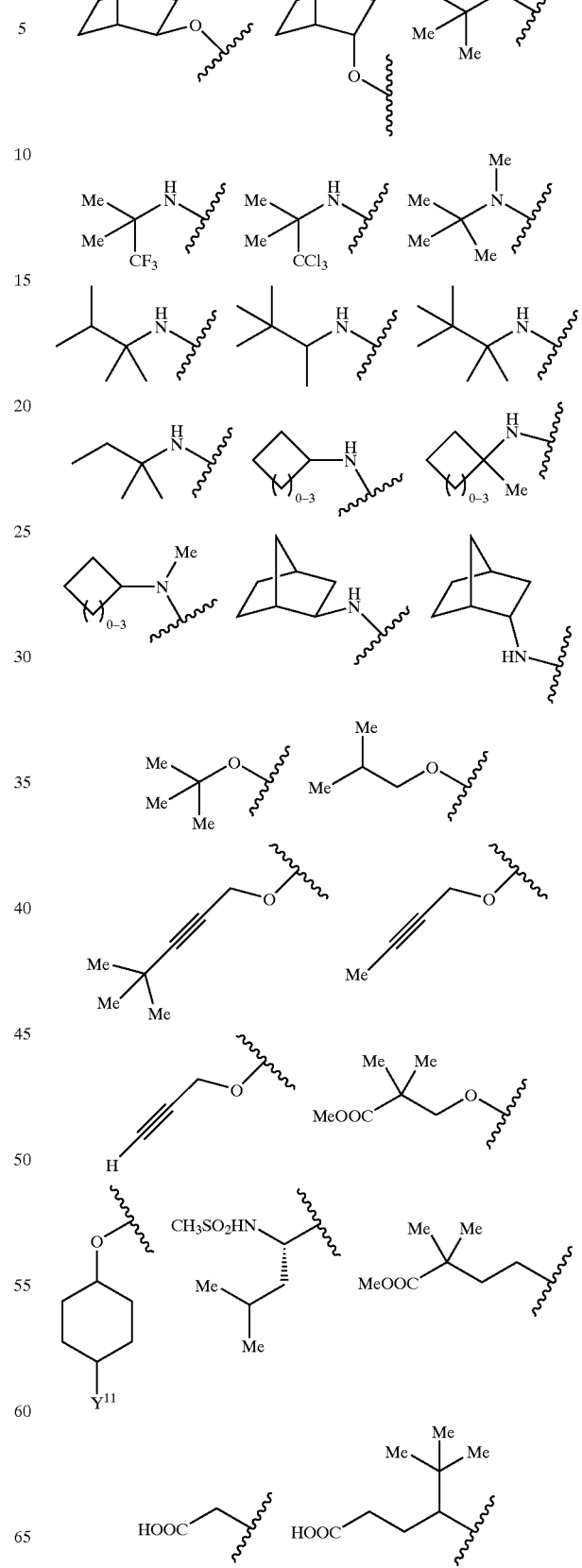

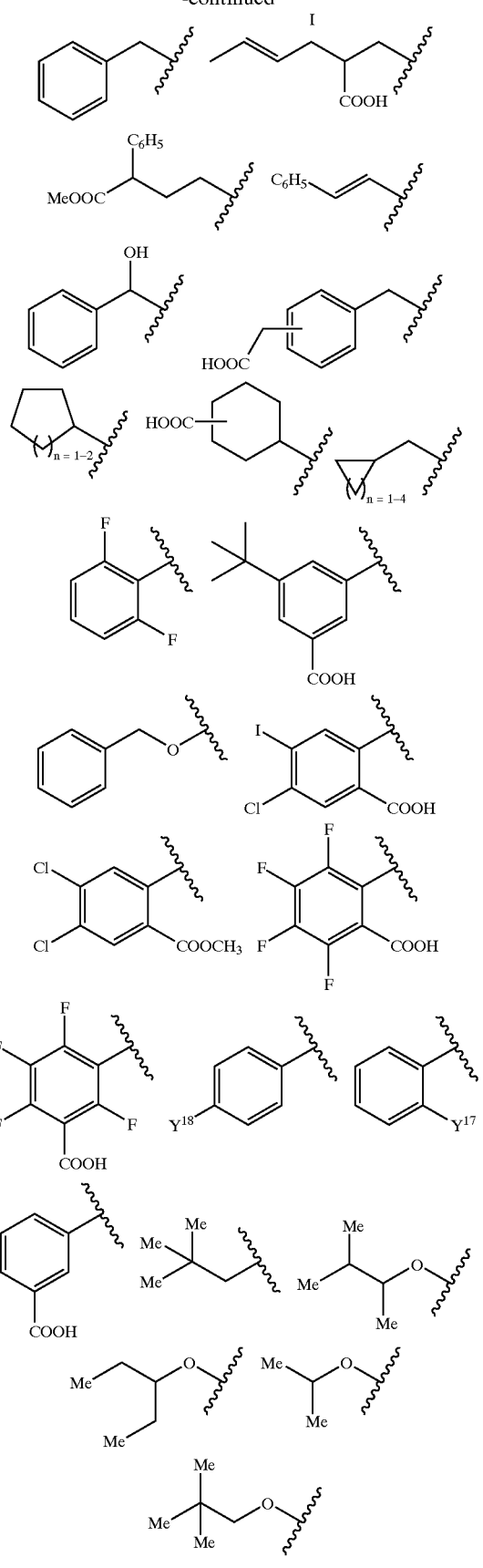
Wherein:
$Y^{17}$=CF$_3$, CONH$_2$, OH, NH$_2$, or COOH
$Y^{18}$=F, COOH
Still more preferred moieties for Y are:
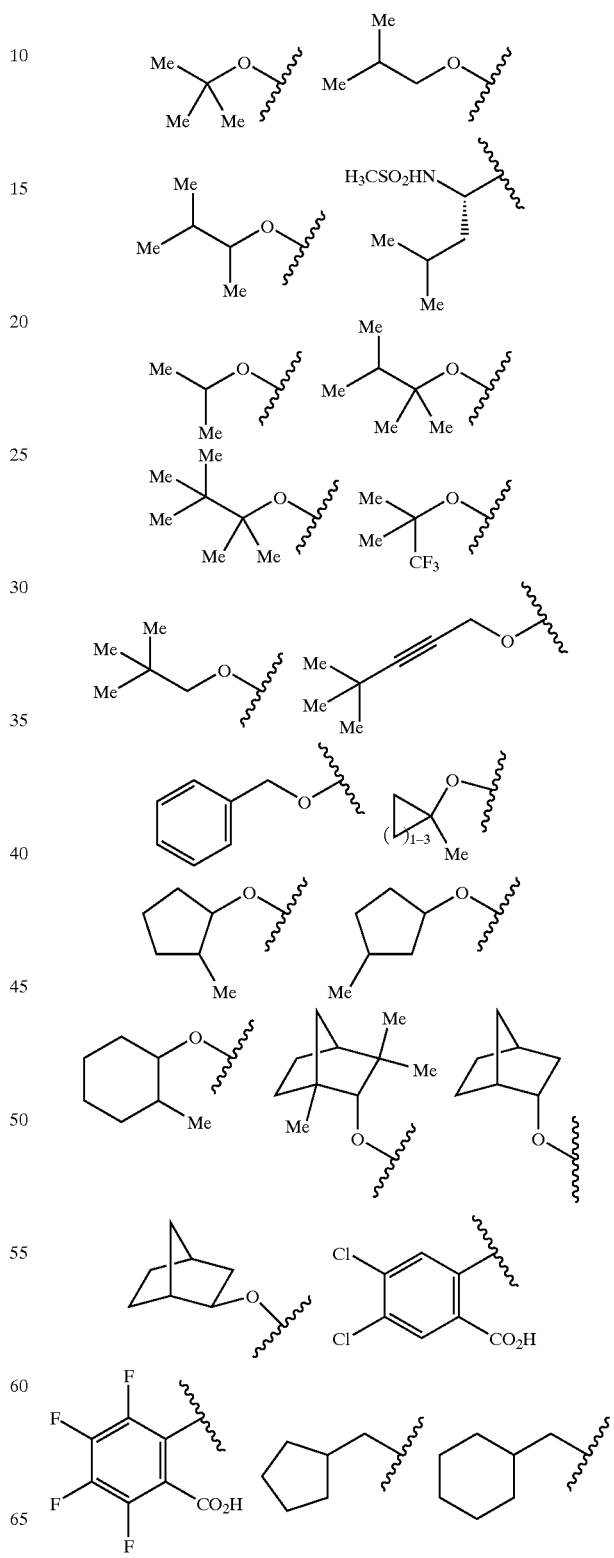

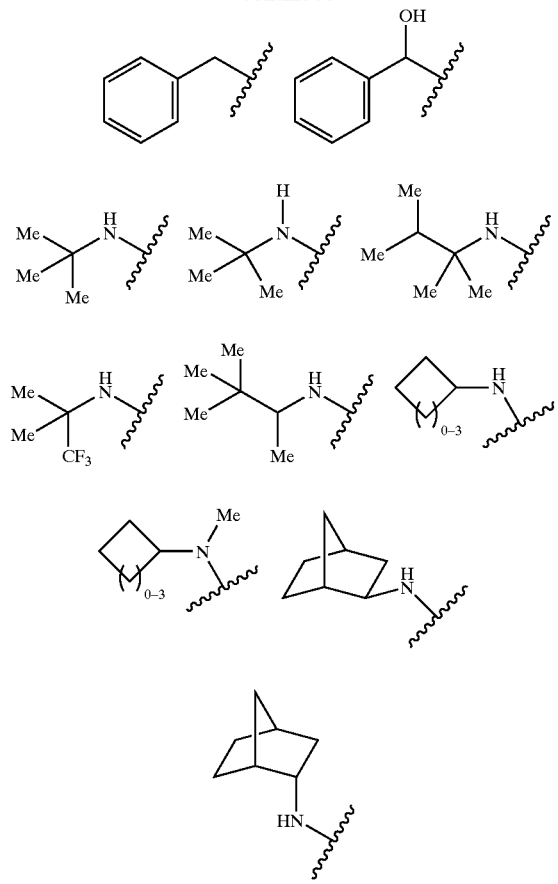

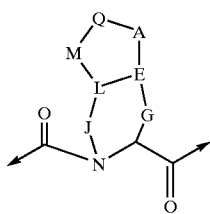

As shown in Formula I and as stated above, the unit:

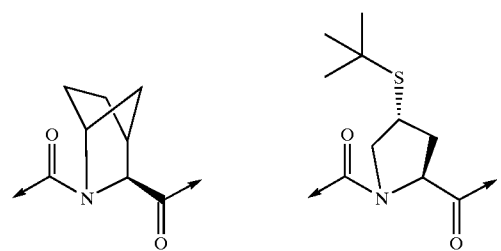

represents a cyclic ring structure, which may be a five-membered or six-membered ring structure. When that cyclic ring represents a five-membered ring, it is a requirement of this invention that that five-membered cyclic ring does not contain a carbonyl group as part of the cyclic ring structure. Preferably, the above mentioned cyclic ring structure is selected from the following structures:

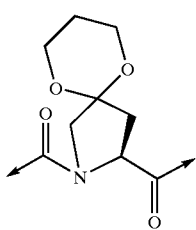

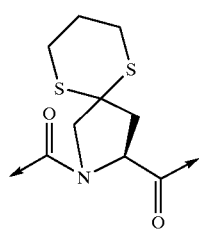

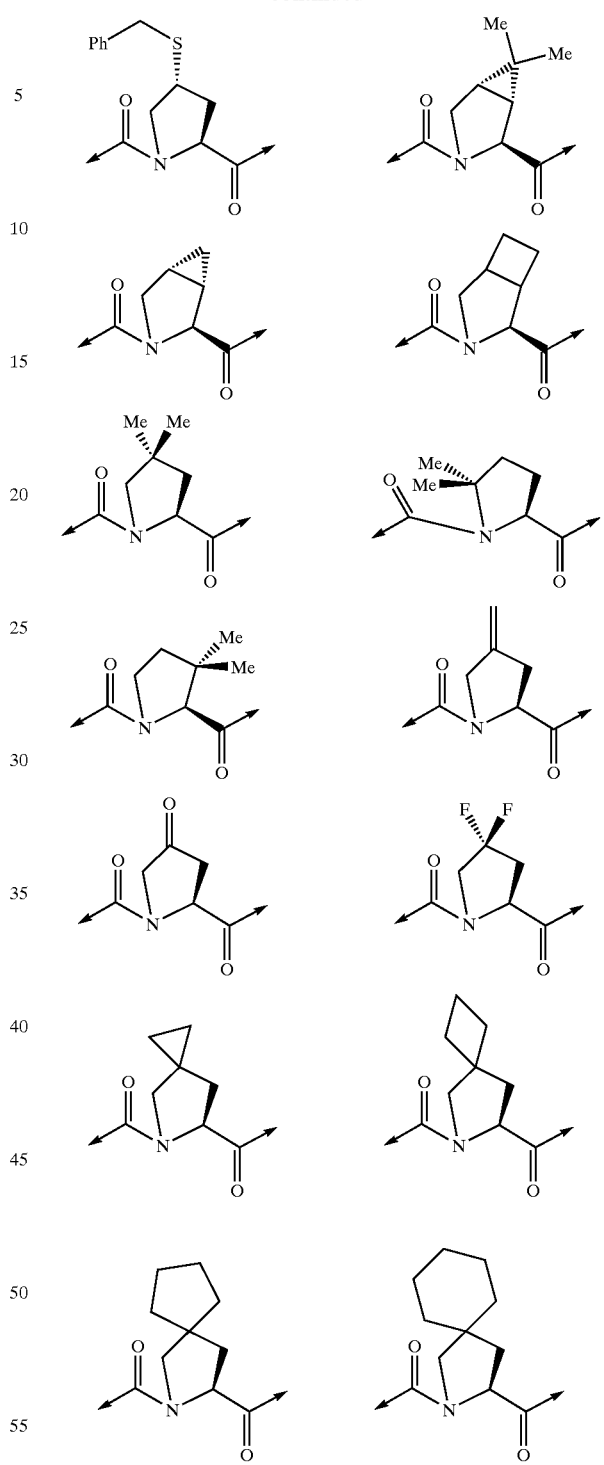

-continued
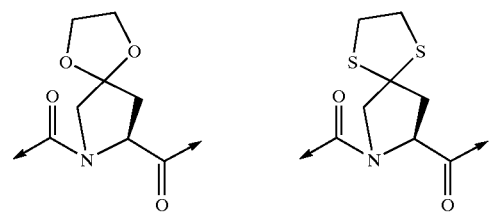
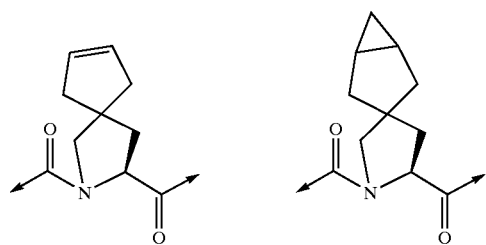
Additionally, the cyclic ring structure
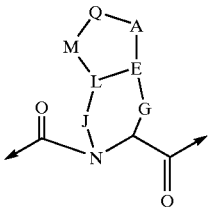
is selected from the following structures:
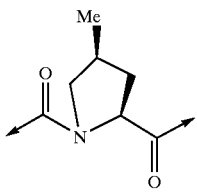 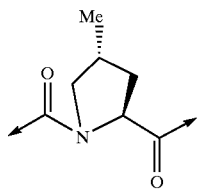
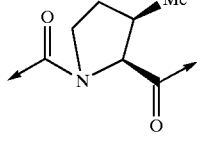 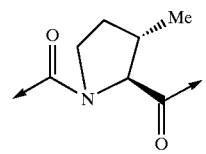
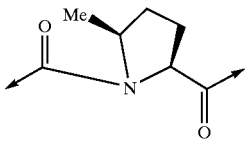
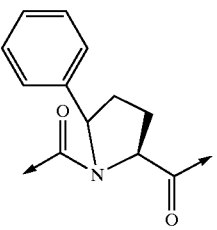 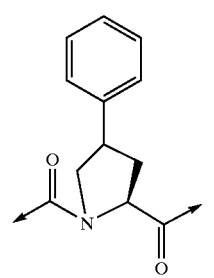
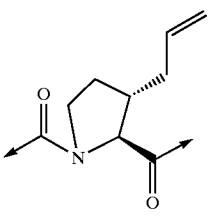 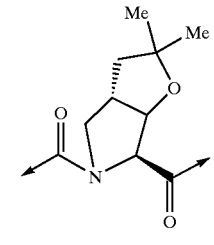
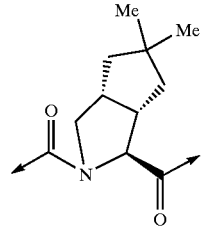 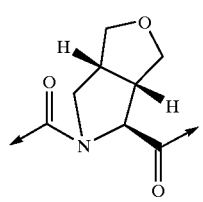

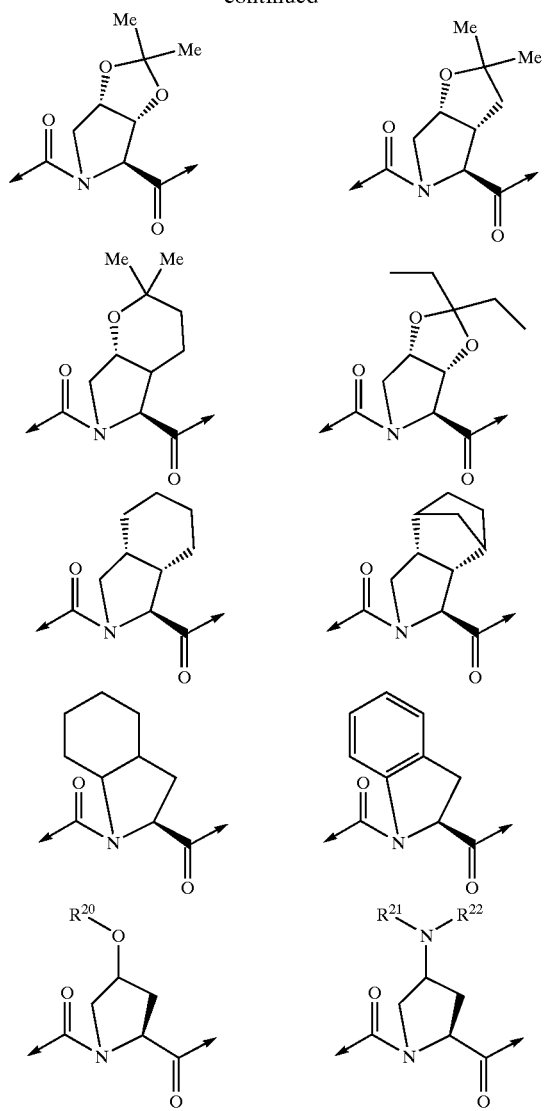
where R²⁰ is selected from the following moieties:
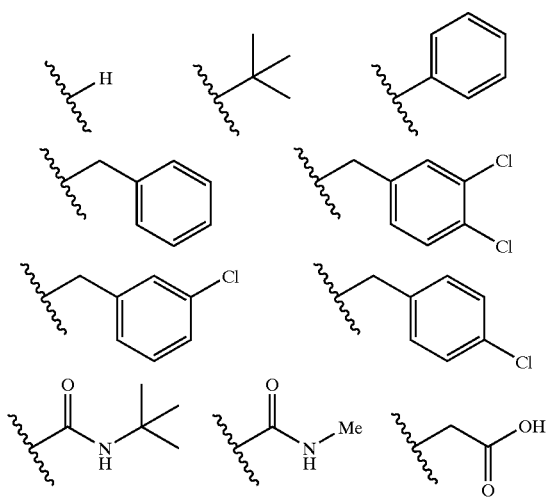
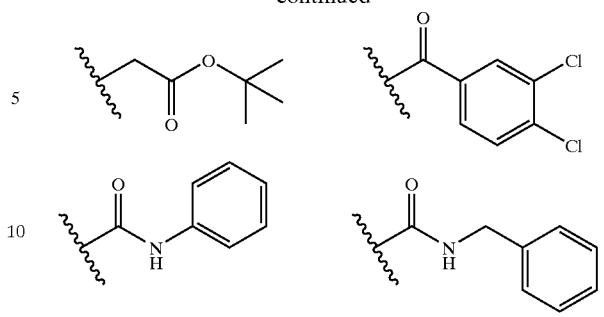
R²¹ and R²² can be the same or different and are independently selected from the following moieties:
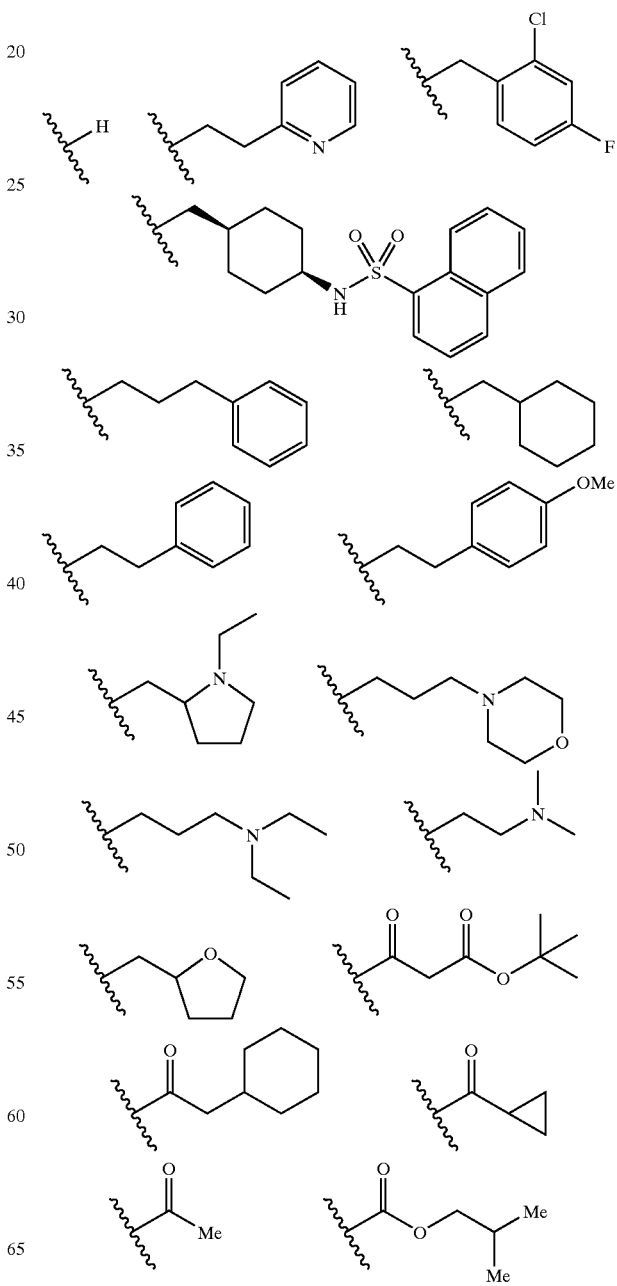

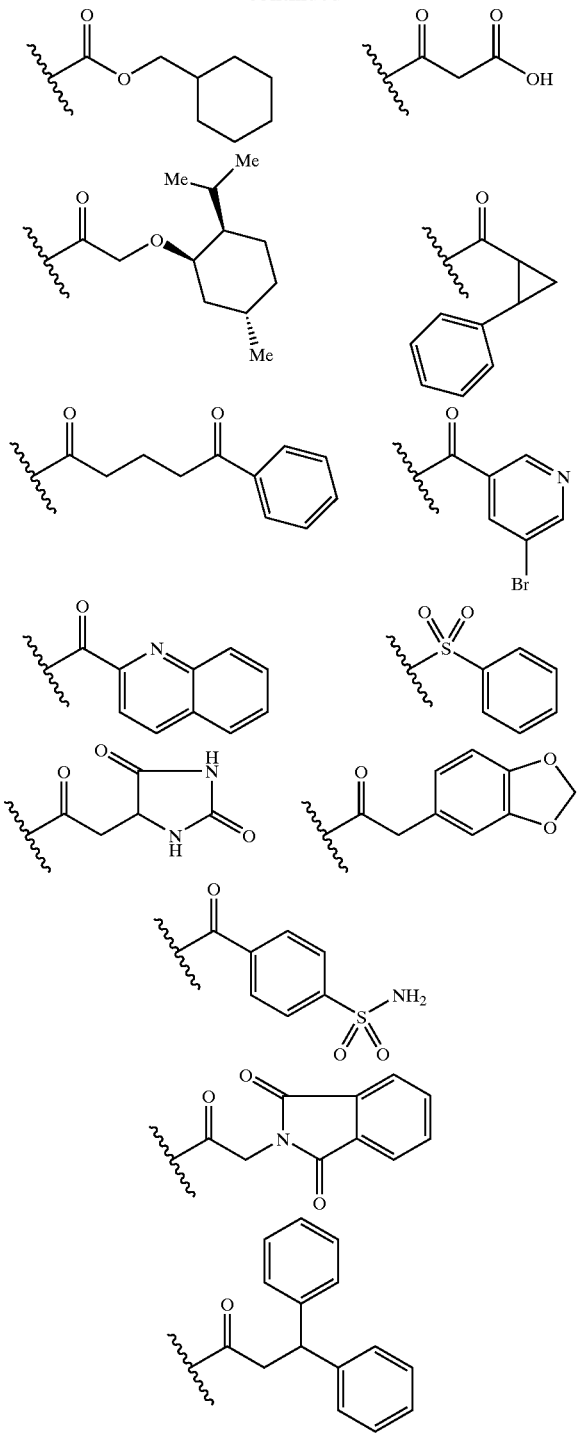

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched.

"Aryl" means an aromatic monocyclic or multicyclic ring system comprising about 6 to about 14 carbon atoms, preferably about 6 to about 10 carbon atoms. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, N-oxide of pyridyl, pyrazinyl, furanyl (furyl), thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,5-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halogen" or "halo" means fluorine, chlorine, bromine, or iodine.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiazolidinyl, 1,4-dioxanyl, tetrahydrofuranyl, tetrahydrothiophenyl, and the like.

The term "heteroaralkyl" or "heteroarylalkyl" means a heteroaryl-alkyl- group in which the heteroaryl and alkyl are as previously described. Preferred heteroarylalkyls comprise a lower alkyl group. Non-limiting examples of suitable heteroarylalkyl groups include pyridin-4-ylmethyl, thien-3-ylmethyl and the like. The bond to the parent moiety is through the alkyl.

The term "heterocyclylalkyl" means a heterocyclyl-alkyl-group in which the heterocyclyl and alkyl are as previously described. Preferred heterocyclylalkyls comprise a lower alkyl group. Non-limiting examples of suitable heterocyclylalkyl groups include piperidin-4-ylmethyl, pyrrolidin-3-ylmethyl and the like. The bond to the parent moiety is through the alkyl.

"Alkylamino" means an —$NH_2$ or —$NH_3^+$ group in which one or more of the hydrogen atoms on the nitrogen is replaced by an alkyl group as defined above.

"Arylamino" means an —$NH_2$ or —$NH_3^+$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent. Non-limiting examples of suitable substituents (unless specified otherwise) include, for example, halo, alkyl, aryl, cycloalkyl, cyano, hydroxy, alkoxy, alkylthio, amino, —NH (alkyl), —NH(cycloalkyl), —N(alkyl)$_2$, carboxyl, —C(O) O-alkyl, heteroaryl, aralkyl, alkylaryl, aralkenyl, heteroaralkyl, alkylheteroaryl, heteroaralkenyl, hydroxyalkyl, aryloxy, aralkoxy, acyl, aroyl, nitro, aryloxycarbonyl, aralkoxycarbonyl, alkylsulfonyl, arylsulfonyl, heteroarylsulfonyl, alkylsulfinyl, arylsulfinyl, heteroarylsulfinyl, arylthio, heteroarylthio, aralkylthio, heteroaralkylthio, cycloalkenyl, heterocyclyl, heterocyclenyl, $Y_1Y_2$N-alkyl-, $Y_1Y_2$NC(O)— and $Y_1Y_2NSO_2$—, wherein $Y_1$ and Y2 can be the same or different and are independently selected from the group consisting of hydrogen, alkyl, aryl, and aralkyl.

The term "optionally substituted" means optional substitution with the specified groups, radicals or moieties.

As used herein, the term "composition" is intended to encompass a product comprising the specified ingredients in the specified amounts, as well as any product which results, directly or indirectly, from combination of the specified ingredients in the specified amounts.

It should also be noted that any heteroatom with unsatisfied valences in the text, schemes, examples, structural formulae, and Tables herein is assumed to have the hydrogen atom or atoms to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula III or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting NS3/NS4 serine protease and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1–19; P. Gould, *International J. of Pharmaceutics* (1986) 33 201–217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts-are intended to be pharmaceutically acceptable salts within the scope of the invention and all acid and base salts are considered equivalent to the free forms of the corresponding compounds for purposes of the invention.

Compounds of Formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

The invention also provides methods for preparing compounds of Formula I, as well as methods for treating diseases such as, for example, HCV, AIDS (Acquired Immune Deficiency Syndrome), and related disorders. The methods for treating comprise administering to a patient suffering from said disease or diseases a therapeutically effective amount of a compound of Formula I, or pharmaceutical compositions comprising a compound of Formula I.

Also disclosed is the use of a compound of Formula I for the manufacture of a medicament for treating HCV, AIDS, and related disorders.

Also disclosed is a method of treatment of a hepatitis C virus associated disorder, comprising administering an effective amount of one or more of the inventive compounds.

Also disclosed is a method of modulating the activity of hepatitis C virus (HCV) protease, comprising contacting HCV protease with one or more inventive compounds.

Also disclosed is a method of treating, preventing, or ameliorating one or more symptoms of hepatitis C, comprising administering an effective amount of one or more of the inventive compounds. The HCV protease is the NS3 or NS4a protease. The inventive compounds inhibit such protease. They also modulate the processing of hepatitis C virus (HCV) polypeptide.

A further feature of the invention is pharmaceutical compositions containing as active ingredient at least one compound of Formula I (or its salt, solvate or isomers) together with at least one pharmaceutically acceptable carrier or excipient. Thus, the pharmaceutical compositions generally additionally comprise a pharmaceutically acceptable carrier diluent, excipient or carrier (collectively referred to herein as carriers or carrier materials). Because of their HCV inhibitory activity, such pharmaceutical compositions possess utility in treating hepatitis C and related disorders.

In yet another embodiment, the present invention discloses methods for preparing a pharmaceutical composition comprising at least one of the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid; sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally, intravenously or subcutaneously.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate, stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the pharmaceutical compositions disclosed above for treatment of diseases such as, for example, hepatitis C and the like. The method comprises administering a therapeutically effective amount of the inventive pharmaceutical composition to a patient having such a disease or diseases and in need of such a treatment.

In yet another embodiment, the compounds of the invention may be used for the treatment of HCV in humans in monotherapy mode or in a combination therapy (e.g., dual combination, triple combination etc.) mode such as, for example, in combination with at least one antiviral and/or immunomodulatory agent. Examples of such antiviral and/or immunomodulatory agents include Ribavirin (from Schering-Plough Corporation, Madison, N.J.) and Levovirin™ (from ICN Pharmaceuticals, Costa Mesa, Calif.), VP 50406™ (from Viropharma, Incorporated, Exton, Pa.), ISIS 14803™ (from ISIS Pharmaceuticals, Carlsbad, Calif.), Heptazyme™ (from Ribozyme Pharmaceuticals, Boulder, Colo.), VX 497™ (from Vertex Pharmaceuticals, Cambridge, Mass.), Thymosin™ (from SciClone Pharmaceuticals, San Mateo, Calif.), Maxamine™ (Maxim Pharmaceuticals, San Diego, Calif.), mycophenolate mofetil (from Hoffman-LaRoche, Nutley, N.J.), interferon (such as, for example, interferon-alpha, PEG-interferon alpha conjugates) and the like. "PEG-interferon alpha conjugates" are interferon alpha molecules covalently attached to a PEG molecule. Illustrative PEG-interferon alpha conjugates include interferon alpha-2a (Roferon™, from Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, from Boehringer Ingelheim, Ingelheim, Germany) or consensus interferon as defined by determination of a consensus sequence of naturally occurring interferon alphas (Infergen™, from Amgen, Thousand Oaks, Calif.).

As stated earlier, the invention includes tautomers, rotamers, enantiomers and other stereoisomers of the inventive compounds also. Thus, as one skilled in the art appreciates, some of the inventive compounds may exist in suitable isomeric forms. Such variations are contemplated to be within the scope of the invention.

Another embodiment of the invention discloses a method of making the compounds disclosed herein. The compounds may be prepared by several techniques known in the art. A representative illustrative procedure is outlined in the following reaction scheme, followed by relevant synthetic procedures as Examples. It is to be understood that while the following illustrative scheme and Examples describe certain representative preparations, suitable modifications may be made to the reaction sequences to obtain other compounds covered by this invention. Such variations are contemplated to be within the scope of the invention.

Abbreviations which are used in the Preparative Examples, Schemes and Examples are:

| | |
|---|---|
| PPTS | Pyridinium paratoluene sulfonate |
| TsOH | p-Toluenesulfonic acid |
| DHP | Dihydropyran |
| THP | Tetrahydropyran |
| EDCl | 1-Ethyl-3-(3-dimethyl-aminopropyl)carbodiimide |
| HOOBt | 3-Hydroxy-1,2,3-benzotriazin-4(3H)-one |
| NMM | 4-Methylmorpholine |
| HATU | O-(7-Azabenzotriazol-1-yl)-N,N,N',N'-tetramethyluronium hexafluorophosphate |
| DMSO | Dimethyl sulfoxide |
| Cbz-Cl | Benzylchloroformate |

Boc: tert-butyloxycarbonyl

HOOBt: 3-hydroxy-1,2,3-benzotriazin-4(3H)-one

EDCI: 1-(3-dimethylaminopropyl)-3-ethylcarbodiimide hydrochloride

NMM: 4-methylmorpholine

PyBrop: tris(pyrolidino)bromophosphonium hexafluorophosphate

HATU: [O-(7-azabenzotriazol-1-yl)-1,1,3,3-tetramethyluronium hexafluorophosphate]

iPr₂Net: diisopropylethylamine

Boc-t-Leu-OH: N-Boc-tert-leucine

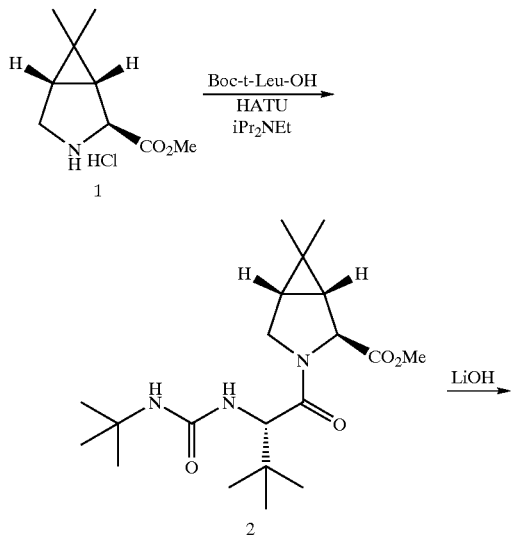

General preparative scheme

41
-continued

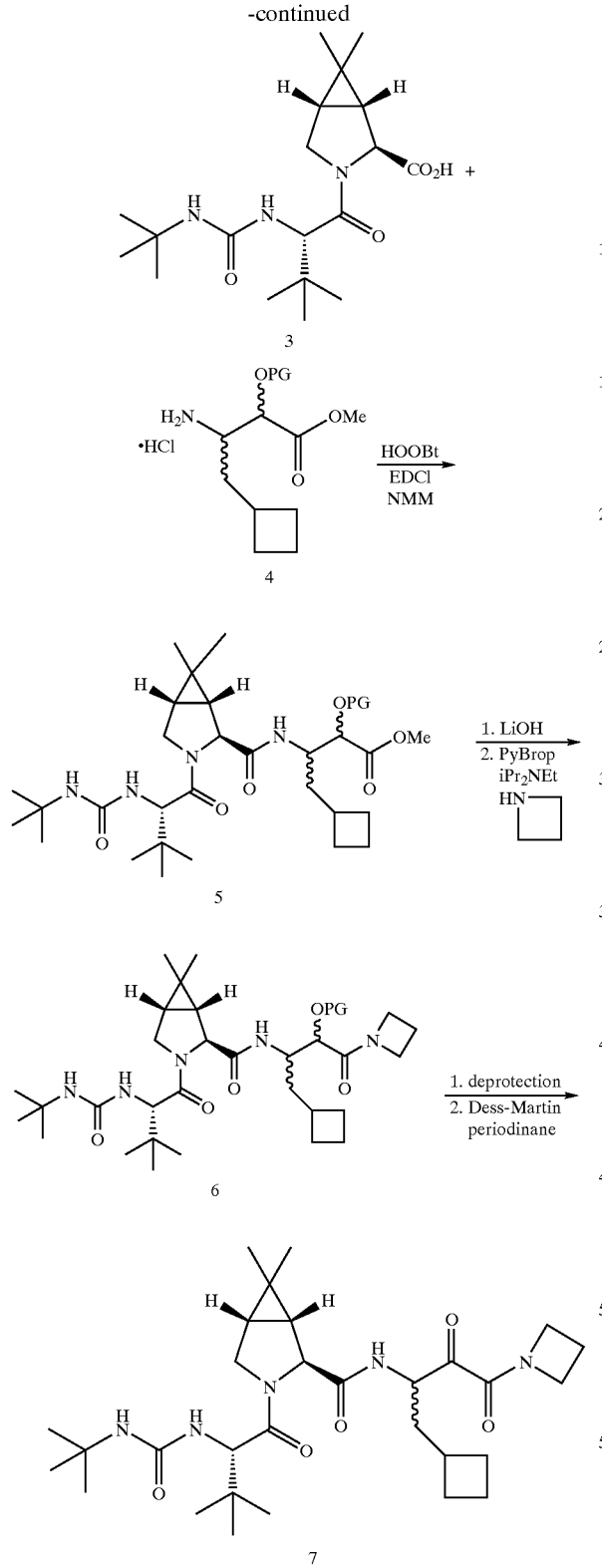

PG is an appropriate protecting group. Non-limiting examples of PG are: tetrahydropyranyl, benzyloxycarbonyl, tert-butyldimethylsilyl. R is as defined in the Summary of invention.

42
EXAMPLES

Example 1

Preparation of Compound of Formula 1

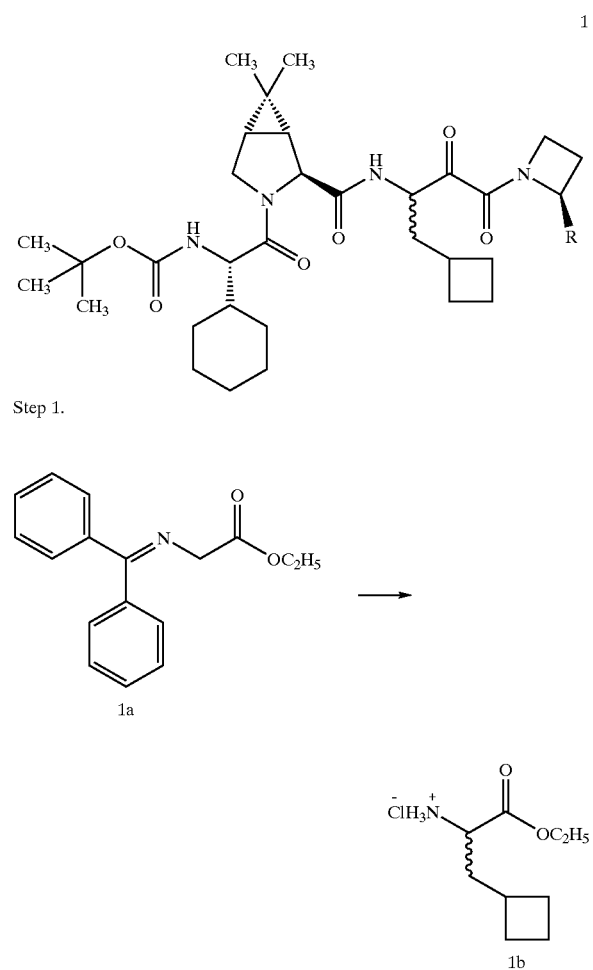

Step 1.

A stirred solution of ketimime 1a (50 g, 187.1 mmol) under $N_2$ in dry THF (400 mL) was cooled to −78° C. and treated with 1 M solution of K-$^t$BuO (220 mL, 1.15 equiv.) in THF. The reaction mixture was warmed to 0° C. and stirred for 1 h and treated with bromomethyl cyclobutane (28 mL, 249 mmol). The reaction mixture was stirred at room temperature for 48 h and concentrated in vacuo. The residue was dissolved in $Et_2O$ (300 mL) and treated with aq. HCl (2 M, 300 mL) The resulting solution was stirred at room temperature for 5 h and extracted with $Et_2O$ (1 L). The aqueous layer was made basic to pH~12–14 with NaOH (50% aq.) and extracted with $CH_2Cl_2$ (3×300 mL). The combined organic layers were dried ($MgSO_4$), filtered, and concentrated to give pure amine (1b, 18 g) as a colorless oil.

Step 2

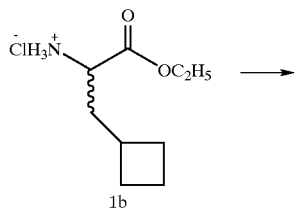

A solution of amine 1b (18 g, 105.2 mmol) at 0° C. in CH$_2$Cl$_2$ (350 mL) was treated with di-tert-butyldicarbonate (23 g, 105.4 mmol) and stirred at rt. for 12 h. After the completion of the reaction (TLC), the reaction mixture was concentrated in vacuo and the residue was dissolved in THF/H$_2$O (200 ml, 1:1) and treated with LiOH.H$_2$O (6.5 g, 158.5 mmol) and stirred at room temperature for 3 h. The reaction mixture was concentrated and the basic aqueous layer was extracted with Et$_2$O. The aqueous layer was acidified with conc. HCl to pH~1–2 and extracted with CH$_2$Cl$_2$. The combined organic layers were dried (MgSO$_4$), filtered, and concentrated in vacuo to yield 1c as a colorless viscous oil which was used for next step without any further purification.

Step 3

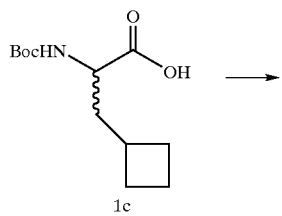

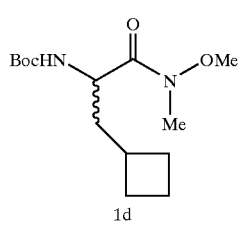

A solution of acid 1c (15.0 g, 62 mmol) in CH$_2$Cl$_2$ (250 mL) was treated with BOP reagent (41.1 g, 93 mmol), N-methyl morpholine (27 mL), N,O-dimethyl hydroxylamine hydrochloride (9.07 g, 93 mmol) and stirred overnight at rt. The reaction mixture was diluted with 1 N aq. HCl (250 mL), and the layers were separated and the aqueous layer was extracted with CH$_2$Cl$_2$ (3×300 ml). The combined organic layers were dried (MgSO$_4$), filtered and concentrated in vacuo and purified by chromatography (SiO$_2$, EtOAc/Hex 2:3) to yield the amide 1d (15.0 g) as a colorless solid.

Step 4

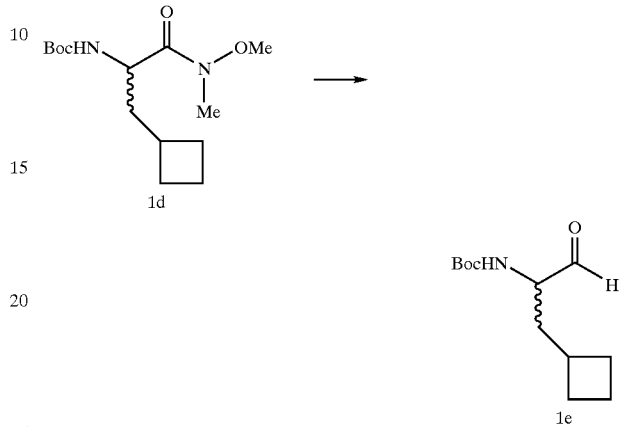

A solution of amide 1d (15 g, 52.1 mmol) in dry THF (200 mL) was treated dropwise with a solution of LiAlH$_4$ (1M, 93 mL, 93 mmol) at 0° C. The reaction mixture was stirred at room temperature for 1 h and carefully quenched at 0° C. with a solution of KHSO$_4$ (10% aq.) and stirred for 0.5 h. The reaction mixture was diluted with aq. HCl (1 M, 150 mL) and extracted with CH$_2$Cl$_2$ (3×200 mL), The combined organic layers were washed with aq. HCl (1 M), saturated NaHCO$_3$, brine, and dried (MgSO$_4$). The mixture was filtered and concentrated in vacuo to yield 1e as a viscous colorless oil (14 g).

Step 5.

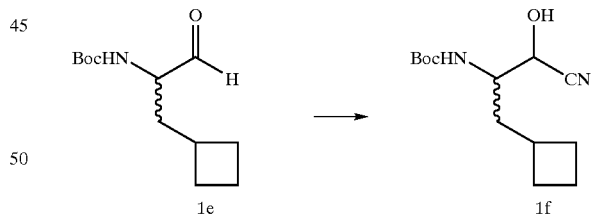

A solution of the aldehyde 1e (14 g, 61.6 mmol) in CH$_2$Cl$_2$ (50 mL), was treated with Et$_3$N (10.73 mL, 74.4 mmol), and acetone cyanohydrin (10.86 g, 127.57 mmol) and stirred at room temperature for 24 hrs. The reaction mixture was concentrated in vacuo and diluted with aq. HCl (1 M, 200 mL) and extracted into CH$_2$Cl$_2$ (3×200 mL). The combined organic layer were washed with H$_2$O, brine, dried (MgSO$_4$), filtered, concentrated in vacuo and purified by chromatography (SiO$_2$, EtOAc/Hex 1:4) to yield 1f (10.3 g) as a colorless liquid.

Step 6

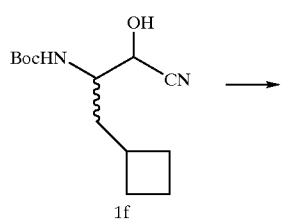

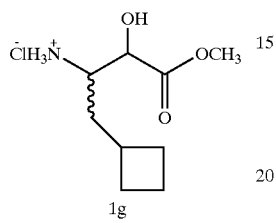

Methanol saturated with HCl*, prepared by bubbling HCl gas to CH₃OH (700 ml) at 0° C., was treated with cyanohydrin 1f and heated to reflux for 24 h. The reaction was concentrated in vacuo to yield 1g, which was used in the next step without purification.

*Alternatively 6M HCl prepared by addition of AcCl to dry methanol can also be used.

Step 7

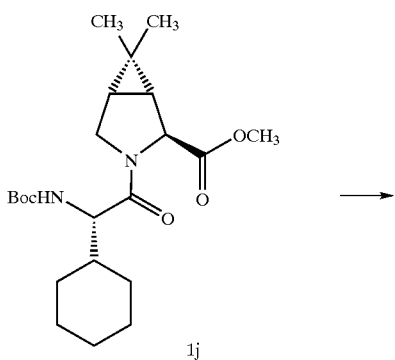

The amino ester 1i was prepared following the method of R. Zhang and J. S. Madalengoitia (*J. Org. Chem.* 1999, 64, 330), with the exception that the Boc group was cleaved by the reaction of the Boc-protected amino acid with methanolic HCl.

A solution of commercial amino acid Boc-Chg-OH, 1h (Senn chemicals, 6.64 g, 24.1 mmol) and amine hydrochloride 1i (4.5 g, 22 mmol) in CH₂Cl₂ (100 mL) at 0° C. was treated with BOP reagent and stirred at rt. for 15 h. The reaction mixture was concentrated in vacuo, then it was diluted with aq. 1 M HCl and extracted into EtOAc (3×200 mL). The combined organic layers were washed with saturated NaHCO₃ (200 mL), dried (MgSO₄), filtered and concentrated in vacuo, and chromatographed (SiO₂, EtOAc/Hex 3:7) to obtain 1jn (6.0 g) as a colorless solid.

Step 8

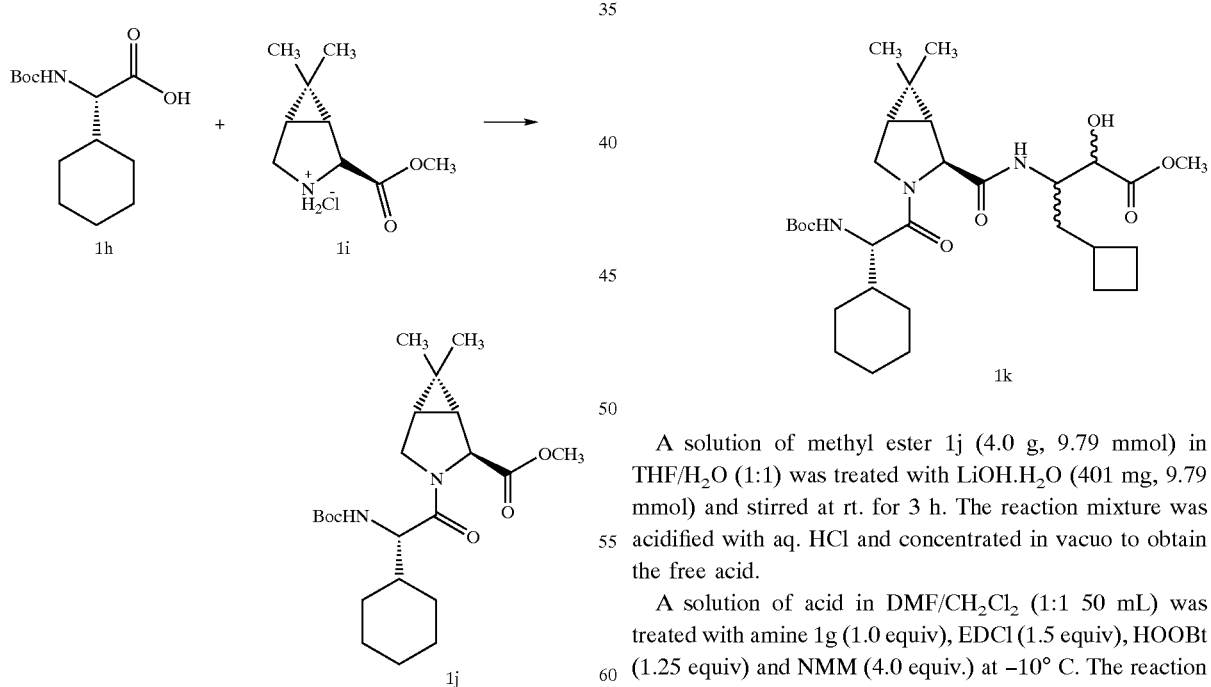

A solution of methyl ester 1j (4.0 g, 9.79 mmol) in THF/H₂O (1:1) was treated with LiOH.H₂O (401 mg, 9.79 mmol) and stirred at rt. for 3 h. The reaction mixture was acidified with aq. HCl and concentrated in vacuo to obtain the free acid.

A solution of acid in DMF/CH₂Cl₂ (1:1 50 mL) was treated with amine 1g (1.0 equiv), EDCl (1.5 equiv), HOOBt (1.25 equiv) and NMM (4.0 equiv.) at −10° C. The reaction mixture was stirred at 0° C. for 48 h and concentrated in vacuo. The residue was diluted with aq. 1M HCl and extracted with CH₂Cl₂, The combined organic layers were extracted with aq. NaHCO₃, aq. HCl, brine, dried (MgSO₄), filtered and concentrated in vacuo to obtain 1k as a tan colored solid.

Step 9.

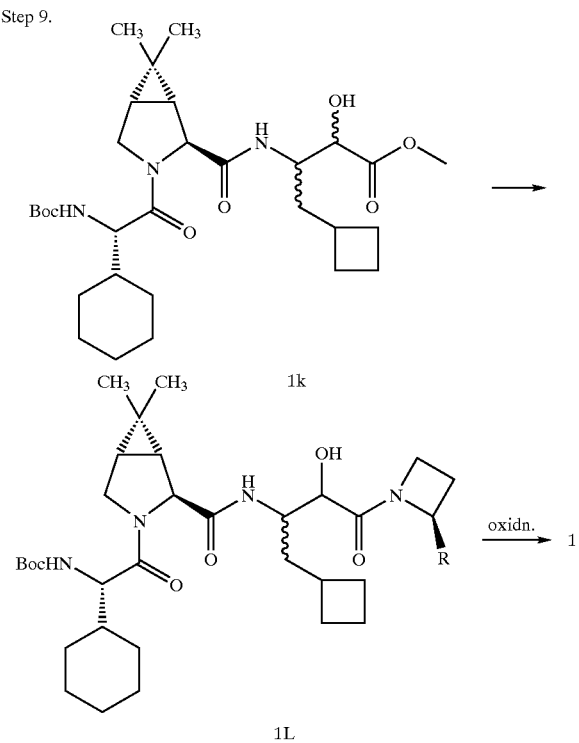

A solution of the ester 1k was hydrolyzed with LiOH (1.5 equiv.) in THF/H$_2$O and concentrated in vacuo. The acid was directly used for coupling with various amines as described below.

A solution of acid (100 mg, 0.19 mmol) in CH$_2$Cl$_2$/DMF (3 mL each) was treated with (S)-aziridine-2-carboxylic acid methyl ester (R=COOCH$_3$, 52 mg, 0.38 mmol), HATU (73 mg, 0.19 mmol) and NMM (63 mg, 0.6 mmol) and stirred at 0° C. for 12 h. The reaction mixture was diluted with CH$_2$Cl$_2$ (100 mL) and washed with aq. HCl (1 M, 100 mL), saturated NaHCO$_3$ (100 mL), brine (100 mL) dried (MgSO$_4$) filtered concentrated in vacuo to give 1L which was used for oxidation.

The hydroxy amide (1L) was taken in CH$_2$Cl$_2$ (5 mL) and treated with Dess Martin reagent (200 mg) and stirred for 3 h at rt. The reaction mixture was diluted with aq. NaHSO$_3$, and aq NaHCO$_3$ (20 mL each) and extracted into CH$_2$Cl$_2$ (100 mL). The combined organic layers were washed with aq. NaHCO$_3$ dried with MgSO$_4$ filtered concentrated in vacuo and purified by chromatography to yield 1 (R=COOCH$_3$, 59 mg) as a colorless amorphous solid.

Some of the compounds prepared by the method described above are shown in Table 1, along with their binding activity.

TABLE 1

| Entry | Structure | Activity |
|---|---|---|
| 1 | 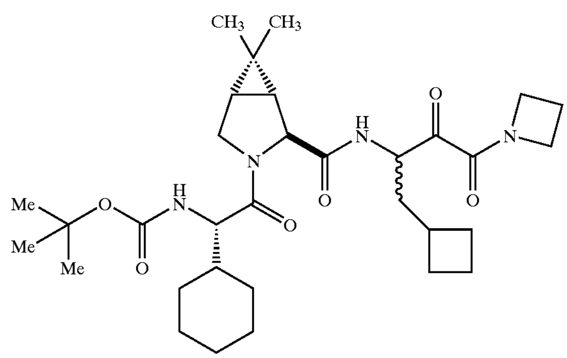 | A |
| 2 | 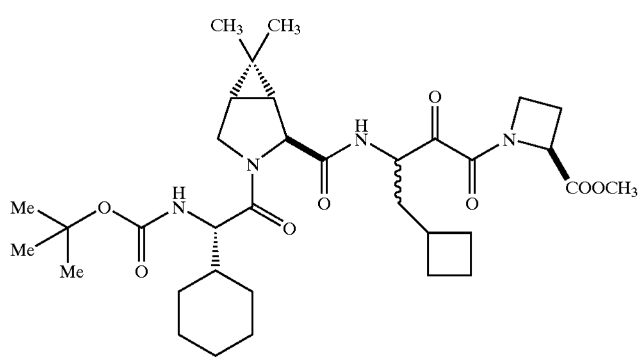 | A |

TABLE 1-continued

| Entry | Structure | Activity |
|---|---|---|
| 3 | 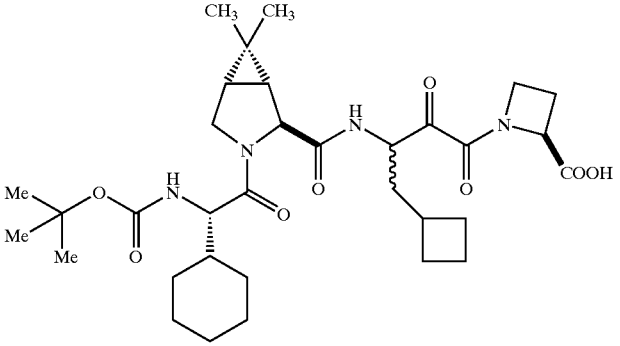 | A |
| 4 | 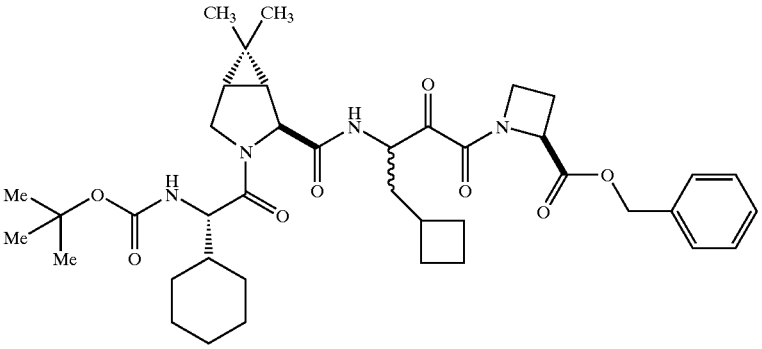 | A |

Binding activity A: <5 μM

Assay for HCV Protease Inhibitory Activity:

Spectrophotometric Assay: Spectrophotometric assay for the HCV serine protease was performed on the inventive compounds by following the procedure described in PCT Publication No. WO 02/08244 published Jan. 31, 2002. The activity of the compounds in Table 1 is shown in the same Table.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound, or enantiomer, stereoisomer, rotamer, tautomer, racemate or prodrug of said compound, or pharmaceutically acceptable salt or solvate of said compound, or pharmaceutically acceptable salt or solvate of said prodrug, said compound having the general structure shown in Formula I:

Formula I

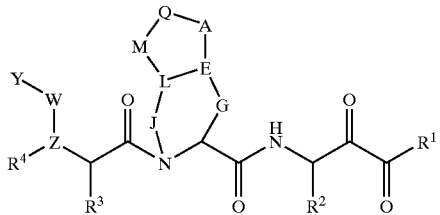

wherein
Y is selected from the group consisting of the following moieties: alkyl, alkyl-aryl, cycloalkyl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino and heterocycloalkylamino, with the proviso that Y maybe optionally substituted with $X^{11}$ or $X^{12}$;

$X^{11}$ is alkyl, alkenyl, alkynyl, cycloalkyl, cycloalkylalkyl, heterocyclyl, heterocyclylalkyl, aryl, alkylaryl, arylalkyl, heteroaryl, alkylheteroaryl, or heteroarylalkyl, with the proviso that $X^{11}$ may be additionally optionally substituted with $X^{12}$;

$X^{12}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxyl, carbalkoxy, carboxamido, alkoxycarbonylamino, alkoxycarbonyloxy, alkylureido, arylureido, halogen, cyano, or nitro, with the proviso that said alkyl, alkoxy, and aryl may be additionally optionally substituted with moieties independently selected from $X^{12}$;

$R^1$ is:

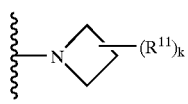

wherein k is a number from 0 to 5, which can be the same or different, $R^{11}$ denotes optional substituents, with each of said substituents being independently selected from the group consisting of alkyl, alkenyl, alkynyl, aryl, cycloalkyl, alkyl-aryl, heteroalkyl, heteroaryl, aryl-heteroaryl, alkyl-heteroaryl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino, heterocycloalkylamino, hydroxy, thio, alkylthio, arylthio, amino, alkylsulfonyl, arylsulfonyl, alkylsulfonamido, arylsulfonamido, carboxyl, carbalkoxy, carboxamido, alkoxycarbonylamino, alkoxycarbonyloxy, alkylureido, arylureido, halogen, cyano, and nitro, with the proviso that $R^{11}$ (when $R^{11} \neq H$) maybe optionally substituted with $X^{11}$ or $X^{12}$;

Z is selected from O, N, CH or CR;

W may be present or absent, and if W is present, W is selected from C=O, C=S;

Q may be present or absent, and when Q is present, Q is CH, N, P, $(CH_2)_p$, $(CHR)_p$, $(CRR')_p$, O, N(R), S, or $S(O_2)$; and when Q is absent, M may be present or absent; when Q and M are absent, A is directly linked to L;

A is O, $CH_2$, $(CHR)_p$, $(CHR—CHR')_p$, $(CRR')_p$, N(R), S, $S(O_2)$ or a bond;

E is CH, N, CR, or a double bond towards A, L or G;

G may be present or absent, and when G is present, G is $(CH_2)_p$, $(CHR)_p$, or $(CRR')_p$; and when G is absent, J is present and E is directly connected to the carbon atom in Formula I as G is shown linked to;

J is $(CH_2)_p$, $(CHR)_p$, or $(CRR')_p$;

L may be present or absent, and when L is present, L is CH, C(R), O, S or N(R); and when L is absent, then M may be present or absent; and if M is present with L being absent, then M is directly and independently linked to E, and J is directly and independently linked to E;

M may be present or absent, and when M is present, M is O, N(R), S, $S(O_2)$, $(CH_2)_p$, $(CHR)_p(CHR—CHR')_p$, or $(CRR')_p$;

p is a number from 0 to 6; and

R, R', $R^2$, $R^3$ and $R^4$ can be the same or different, each being independently selected from the group consisting of H; $C_1$–$C_{10}$ alkyl; $C_2$–$C_{10}$ alkenyl; $C_3$–$C_8$ cycloalkyl; $C_3$–$C_8$ heterocycloalkyl, alkoxy, aryloxy, alkylthio, arylthio, amino, amido, ester, carboxylic acid, carbamate, urea, ketone, aldehyde, cyano, nitro, halogen, (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; and alkyl-aryl;

wherein said alkyl, heteroalkyl, alkenyl, heteroalkenyl, aryl, heteroaryl, cycloalkyl and heterocycloalkyl moieties may be optionally substituted, with said term "substituted" referring to substitution with one or more moieties which can be the same or different, each being independently selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamido, sulfoxide, sulfone, sulfonyl urea, hydrazide, and hydroxamate;

further wherein said unit N-C-G-E-L-J-N represents a five-membered cyclic ring structure with the proviso that when said unit N-C-G-E-L-J-N represents a five-membered cyclic ring structure, or when the bicyclic ring structure in Formula I comprising N, C, G, E, L, J, N, A, Q, and M represents a five-membered cyclic ring structure, then said five-membered cyclic ring structure lacks a carbonyl group as part of said five-membered cyclic ring.

2. The compound of claim 1, wherein $R^1$ is selected from the following:

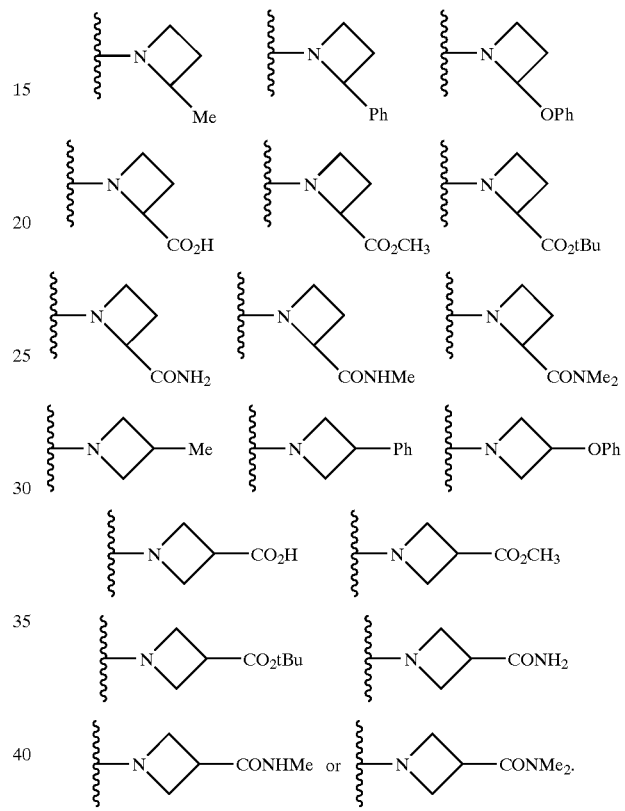

3. The compound of claim 2, wherein $R^3$ is selected from the group consisting of:

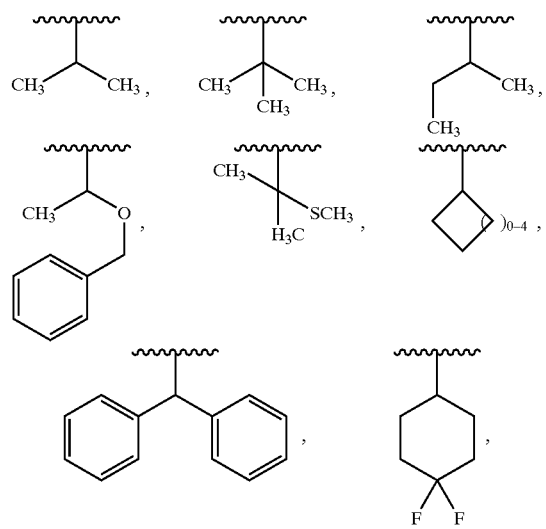

wherein $R^{31}$=OH or O-alkyl;

$R^{51}$=H, COCH$_3$, COOtBu or CONHtBu;

$Y^{19}$ is selected from the following moieties:

and $Y^{20}$ is selected from the following moieties:

4. The compound of claim 3, wherein $R^3$ is selected from the group consisting of the following moieties:

5. The compound of claim 4, wherein Z is N and $R^4$ is H.

6. The compound of claim 5, wherein W is C=O.

7. The compound of claim 6, wherein Y is selected from the following moieties:

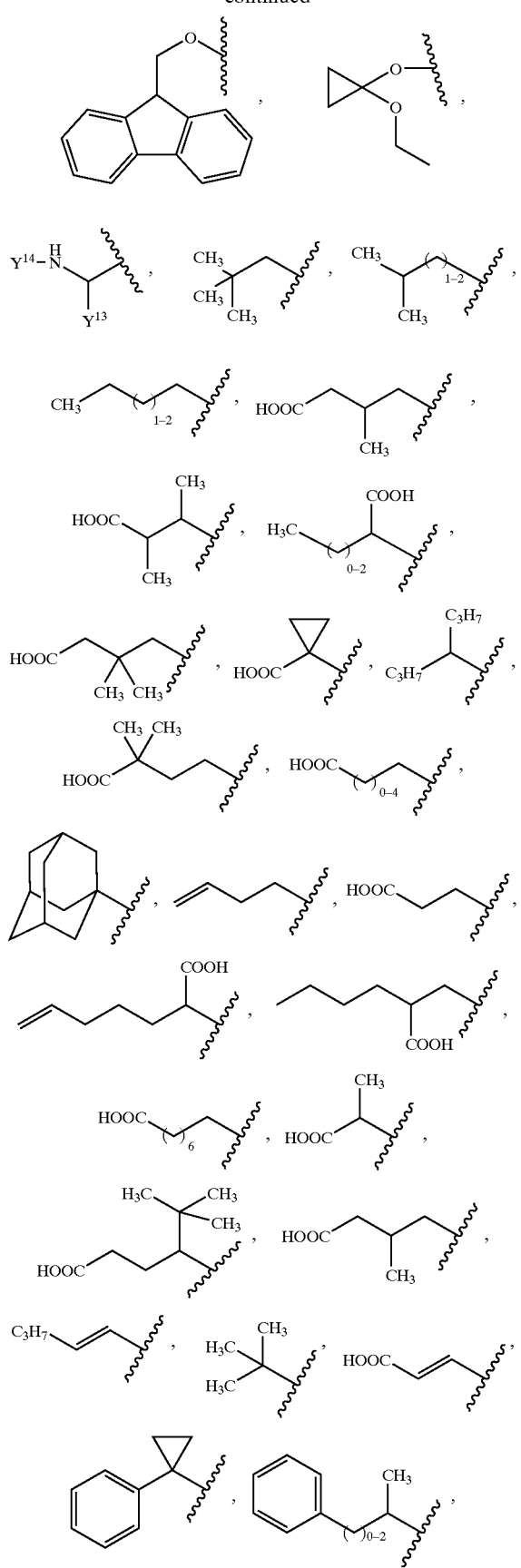
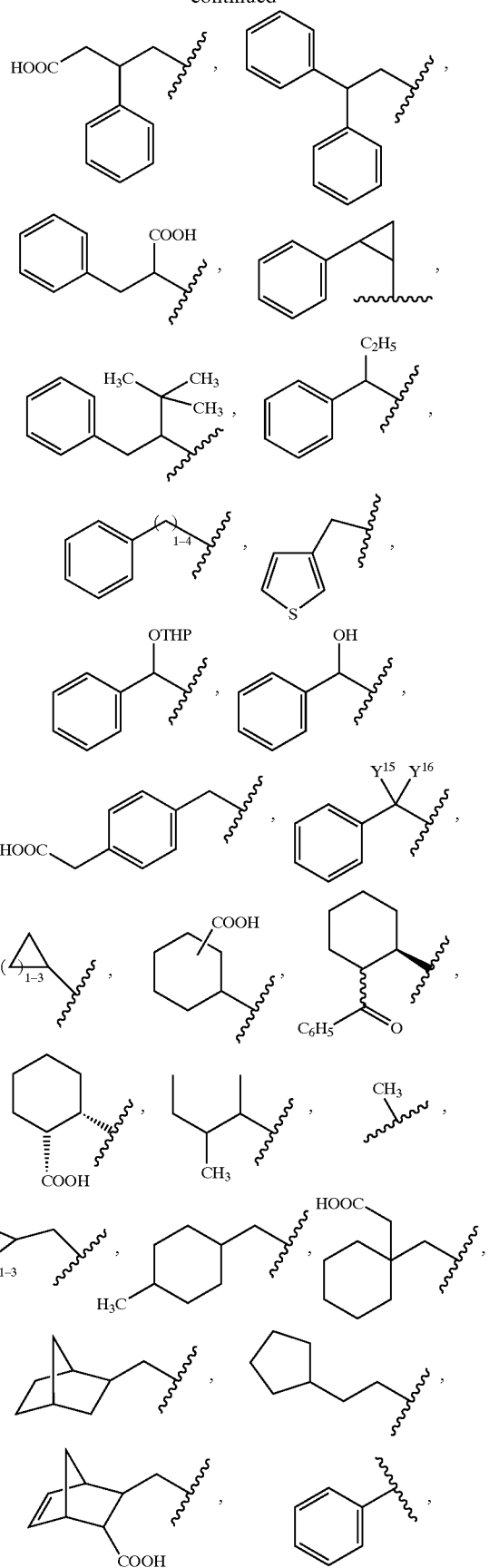

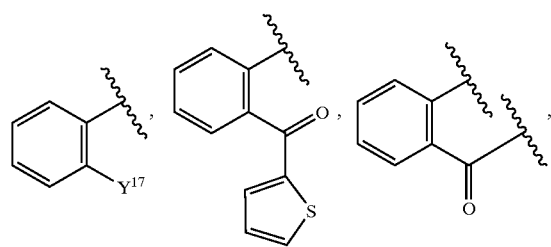
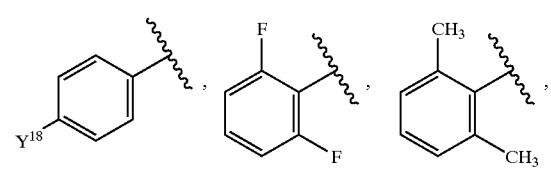
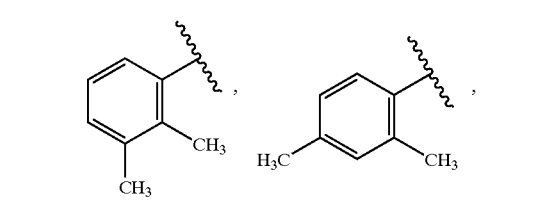
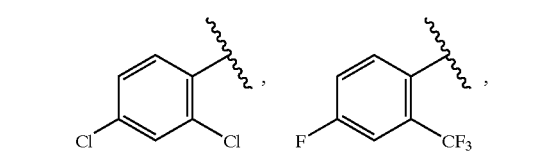
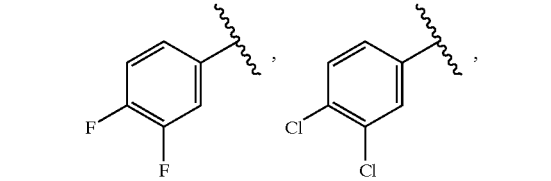
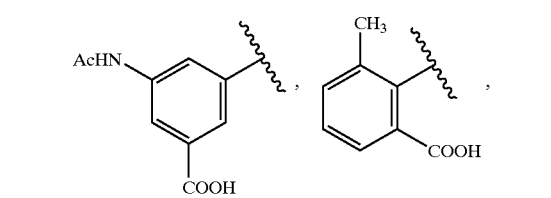
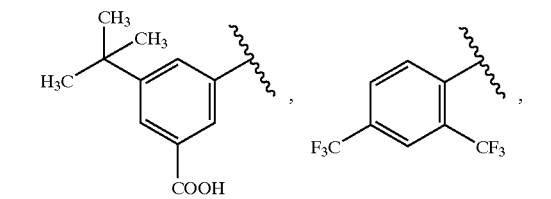
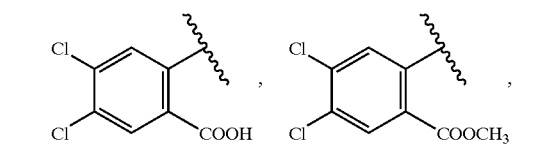
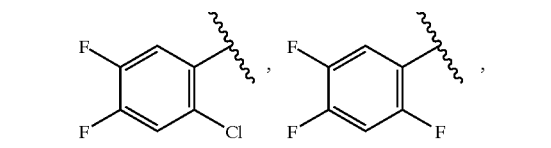
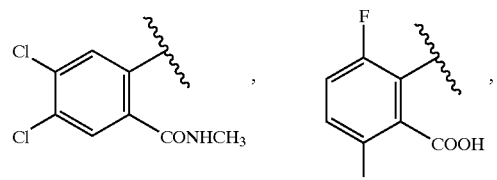
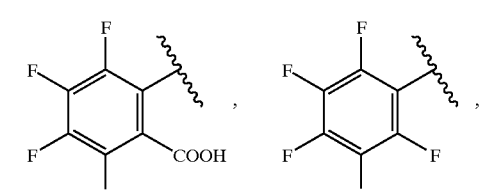
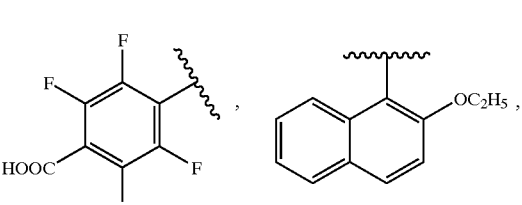
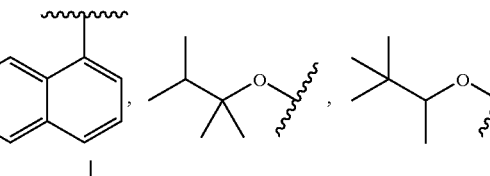
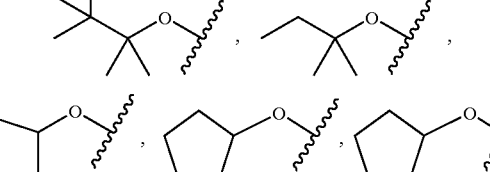
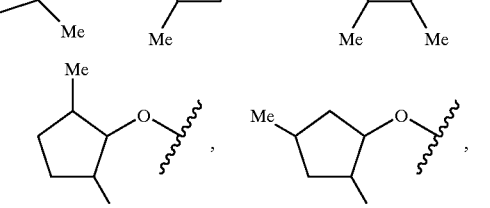
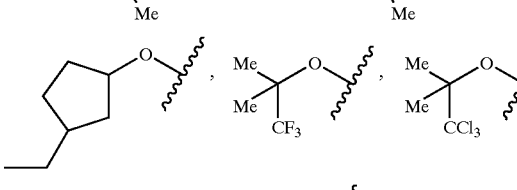
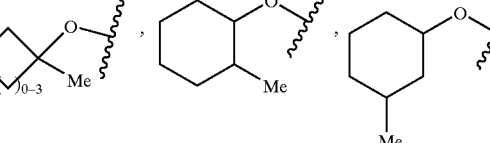
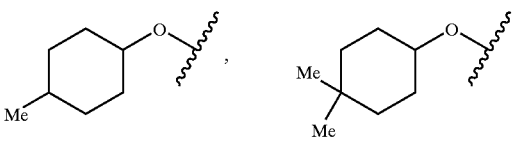

-continued

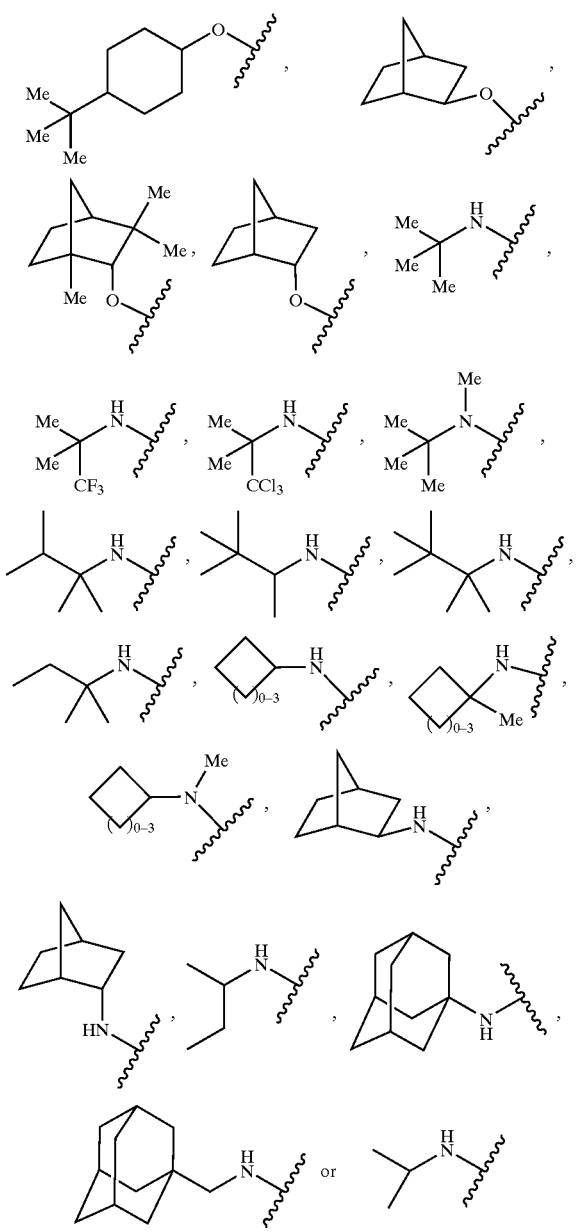

wherein:

$Y^{11}$ is selected from H, COOH, COOEt, OMe, Ph, OPh, NHMe, NHAc, NHPh, CH(Me)$_2$, 1-triazolyl, 1-imidazolyl, and NHCH$_2$COOH;

$Y^{12}$ is selected from H, COOH, COOMe, OMe, F, Cl, or Br;

$Y^{13}$ is selected from the following moieties:

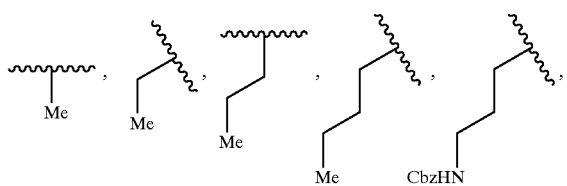

-continued

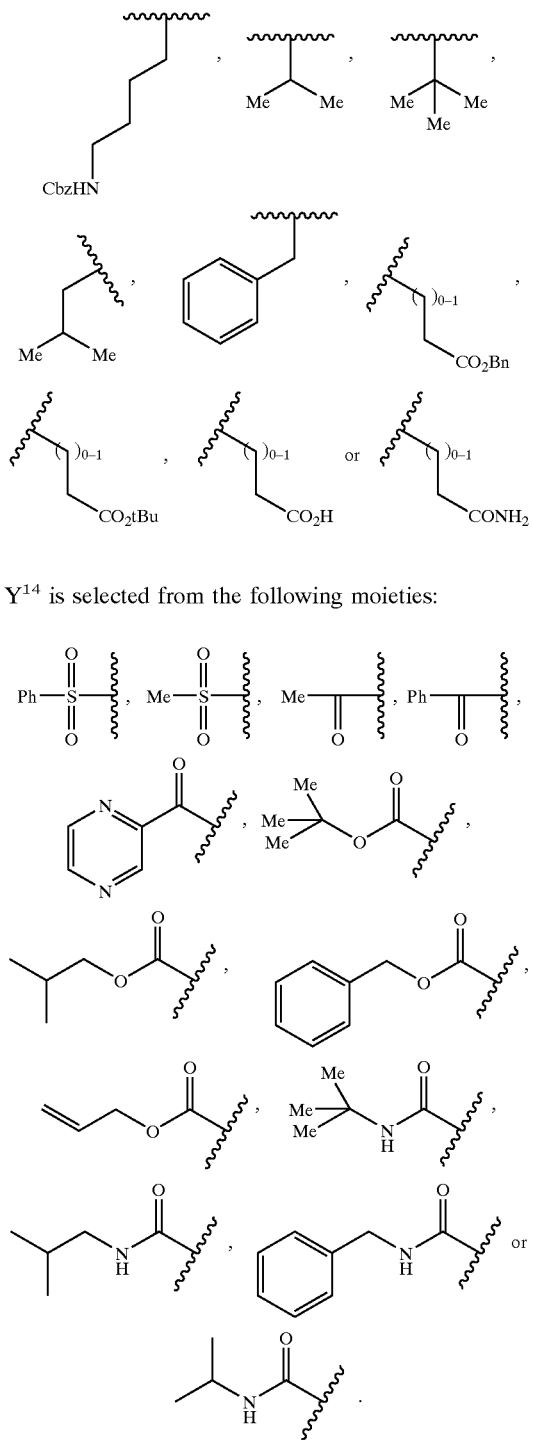

$Y^{14}$ is selected from the following moieties:

$Y^{15}$ and $Y^{16}$ are independently selected from alkyl, aryl, heteroalkyl, and heteroaryl;

$Y^{17}$ is CF$_3$, NO$_2$, CONH$_2$, OH, COOCH$_3$, OCH$_3$, OC$_6$H$_5$, C$_6$H$_5$, COC$_6$H$_5$, NH$_2$, or COOH; and $Y^{18}$ is COOCH$_3$, NO$_2$, N(CH$_3$)$_2$, F, OCH$_3$, CH$_2$COOH, COOH, SO$_2$NH$_2$, or NHCOCH$_3$.

8. The compound of claim 7, wherein Y is selected from the group consisting of:

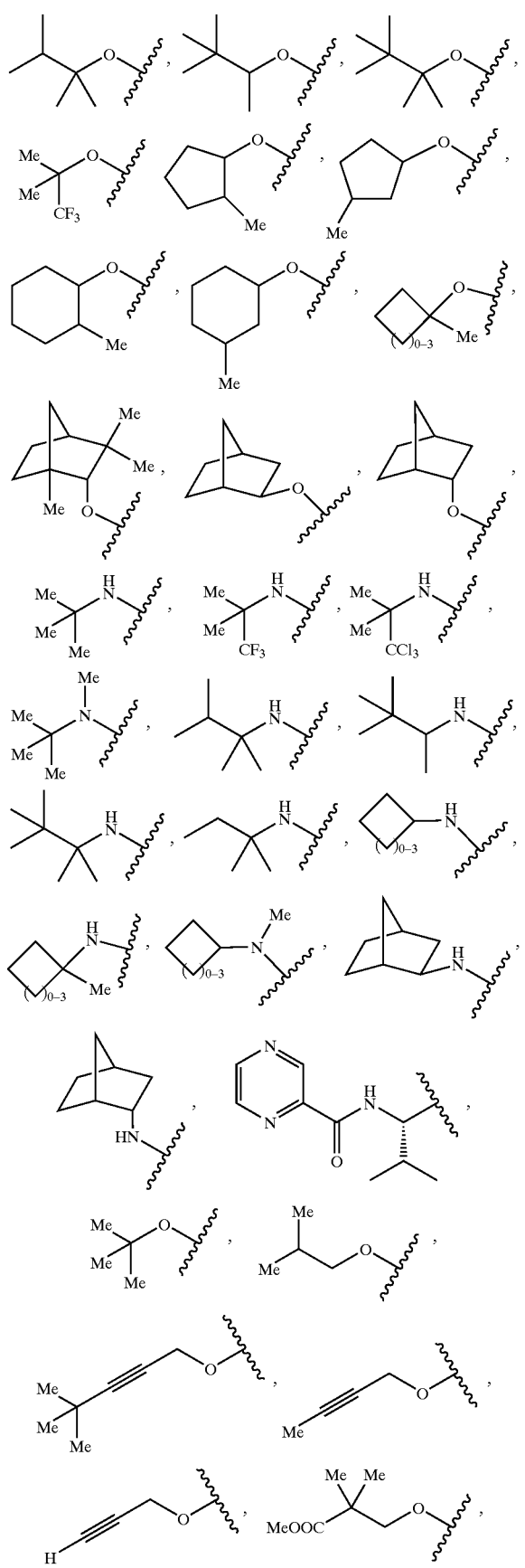
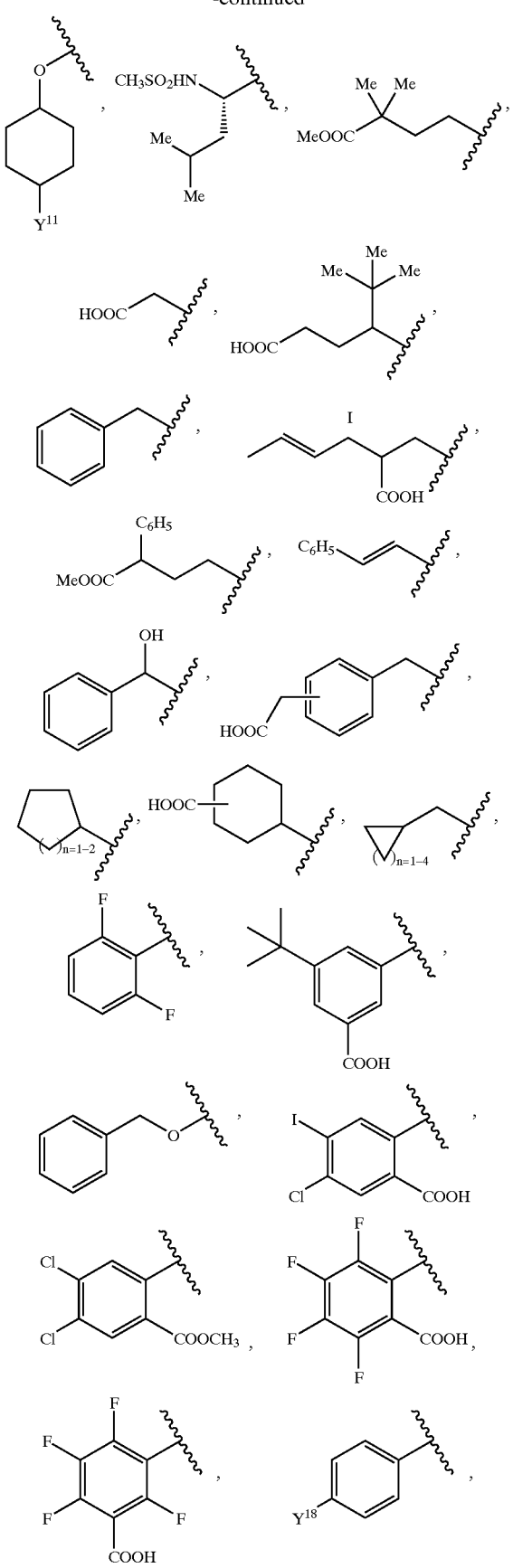

-continued
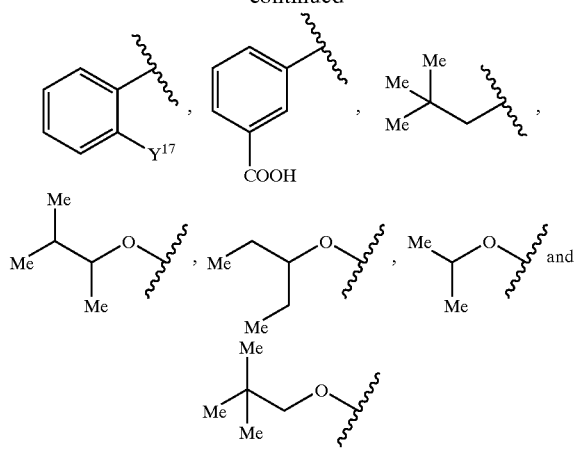
Wherein:
$Y^{17}$=CF$_3$, CONH$_2$, OH, NH$_2$, or COOH
$Y1^8$=F, COOH.
9. The compound of claim 8, wherein Y is selected from the group consisting of:
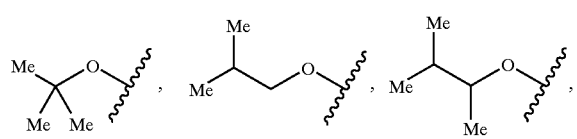
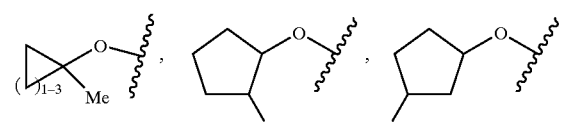
-continued
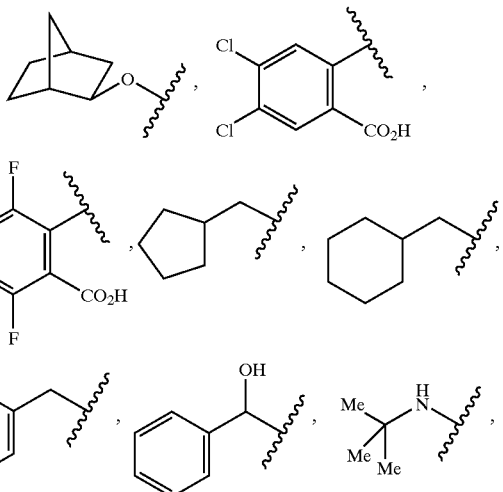
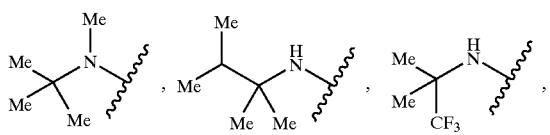
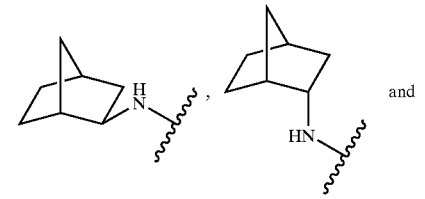
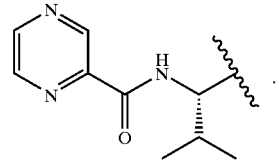
10. The compound of claim 9, wherein R$^2$ is selected from the group consisting of the following moieties:
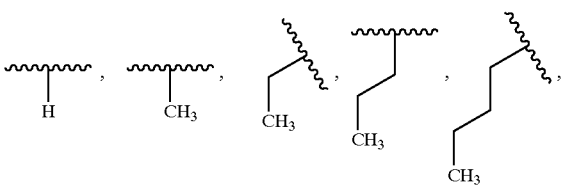
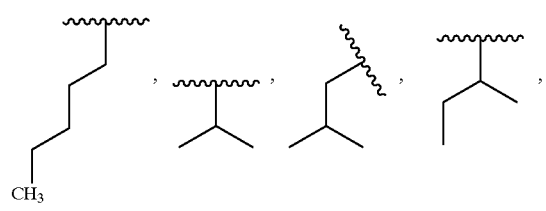

-continued
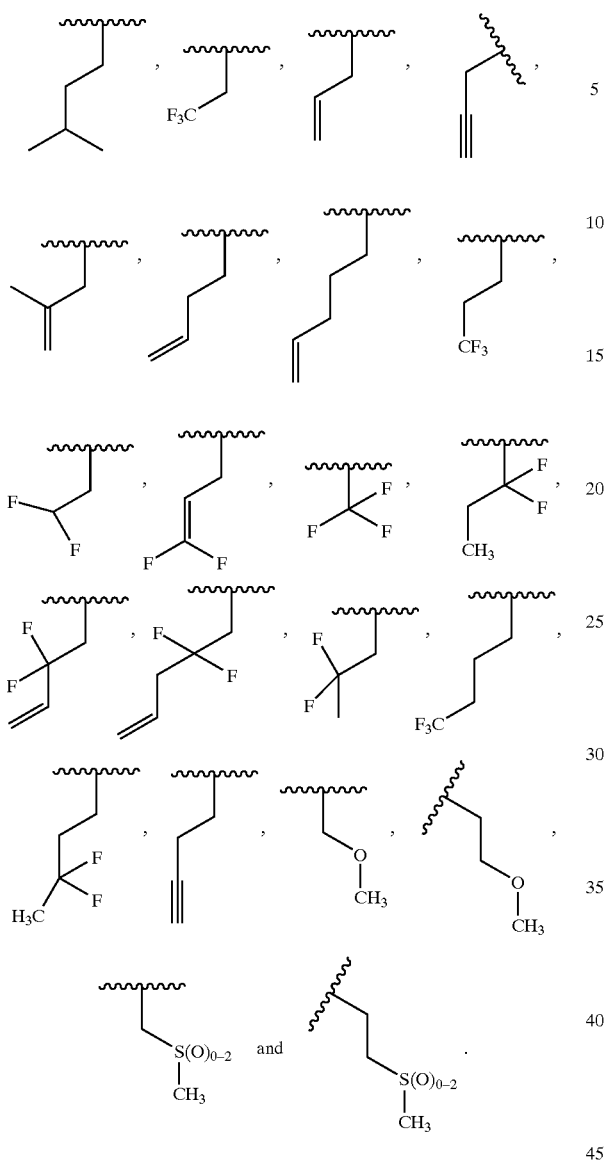
11. The compound of claim 9, wherein $R^2$ is selected from the group consisting of the following moieties:
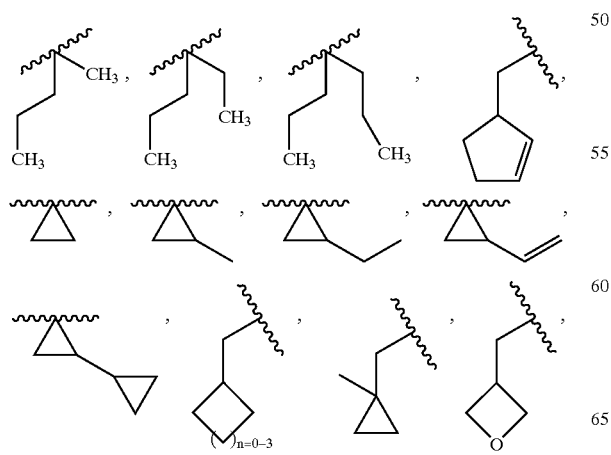
-continued
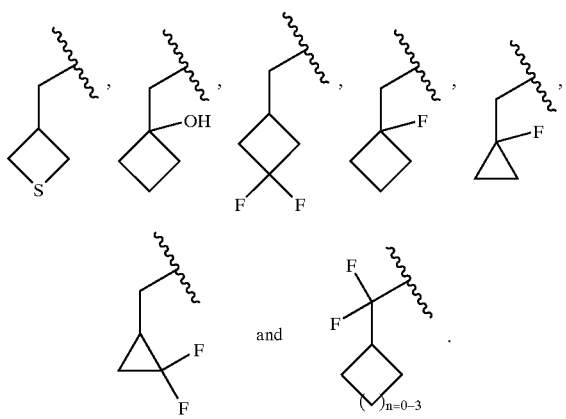
12. The compound of claim 10, wherein the moiety:
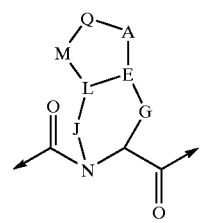
is selected from:
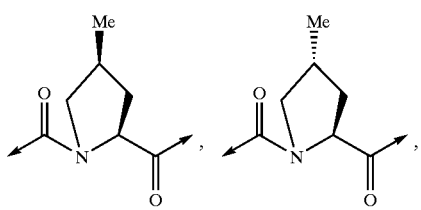
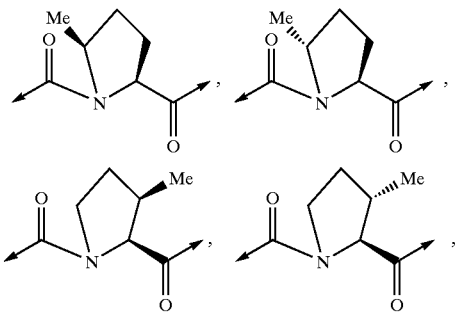
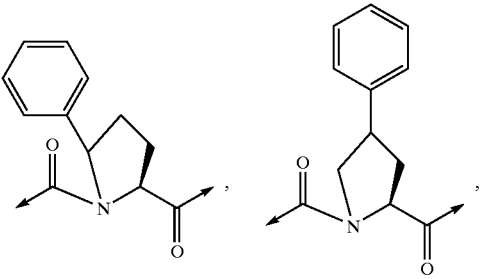

-continued
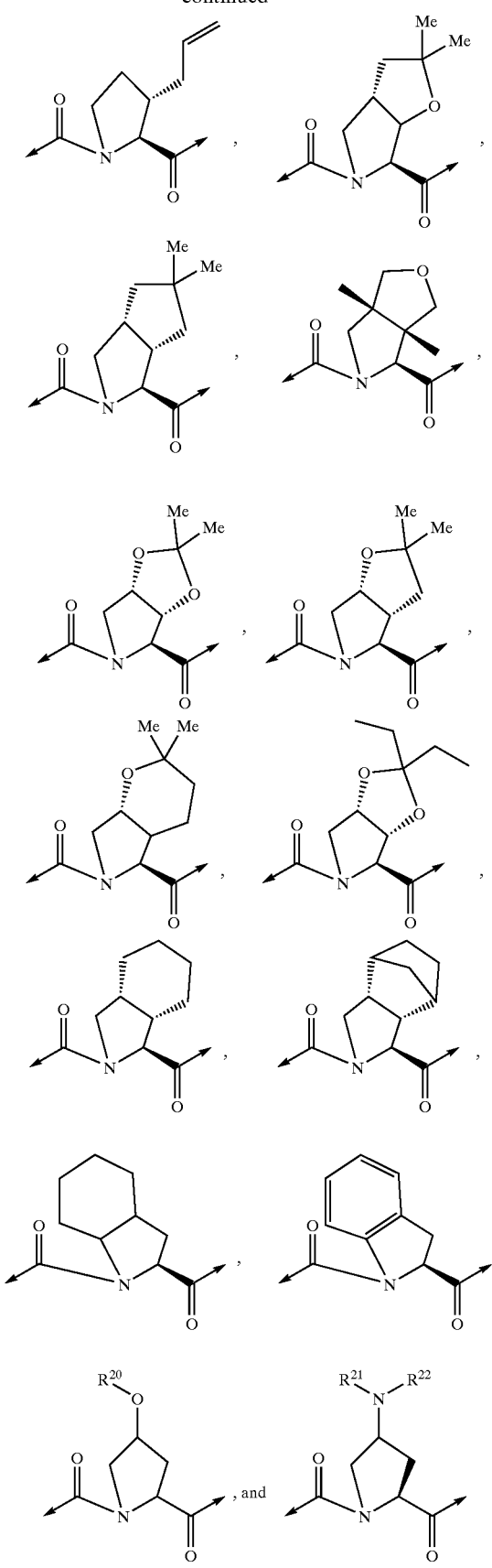
wherein $R^{20}$ is selected from the following structures:
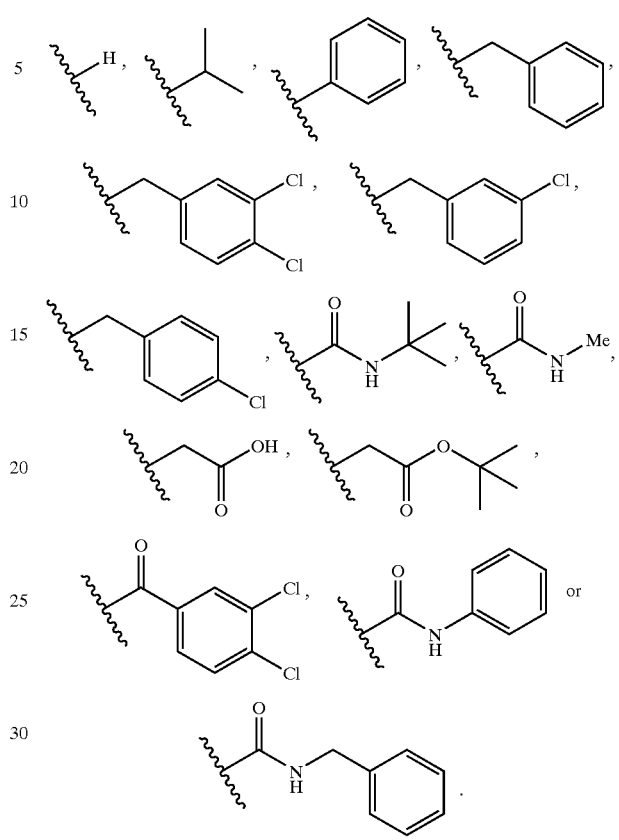
$R^{21}$ and $R^{22}$ may be the same or different and are independently selected from the following structures:
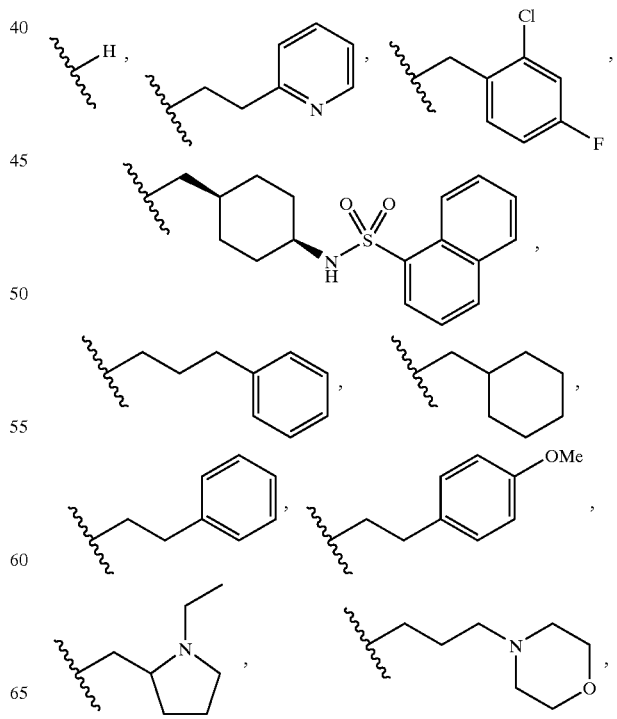

-continued

13. The compound of claim 11, wherein the moiety:

is selected from:

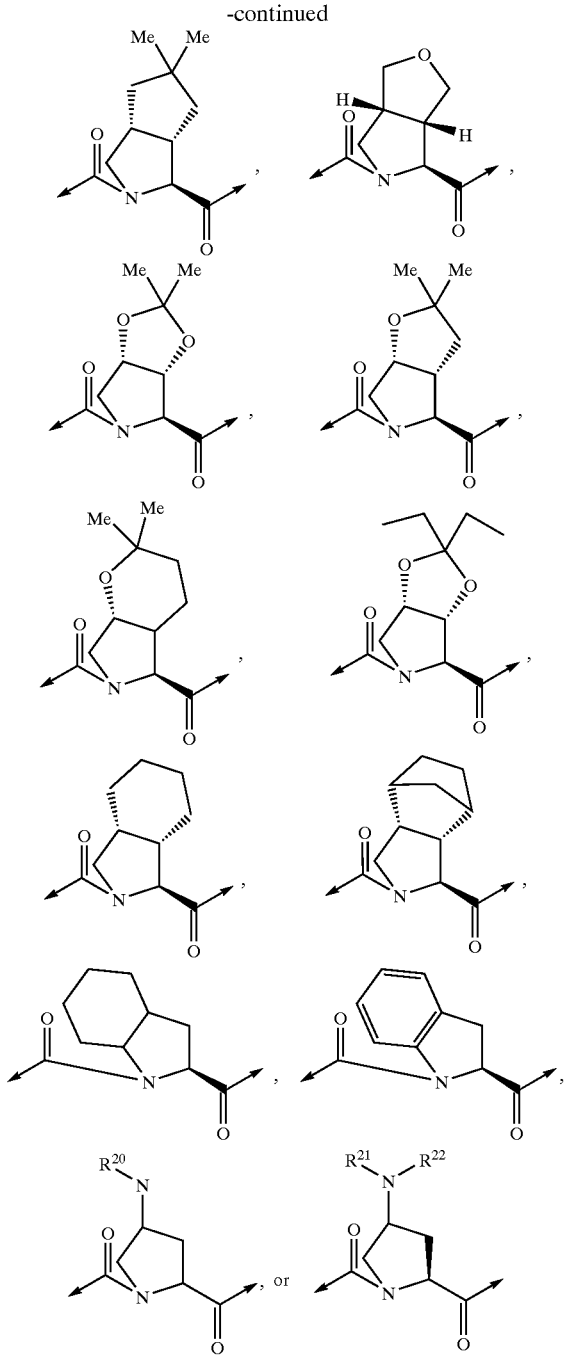
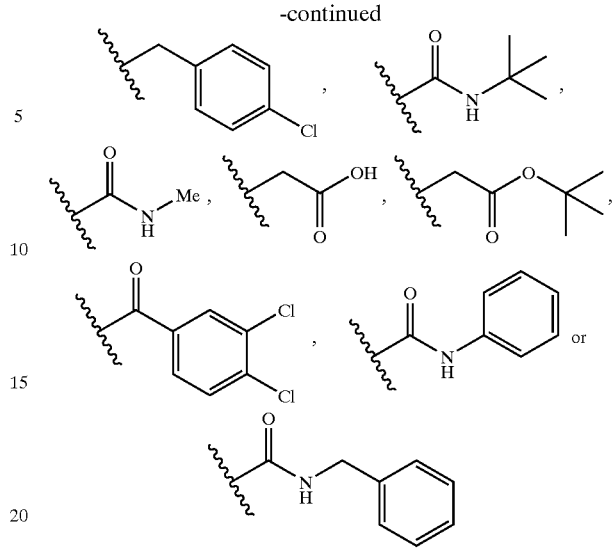
$R^{21}$ and $R^{22}$ may be the same or different and are independently selected from the following structures:
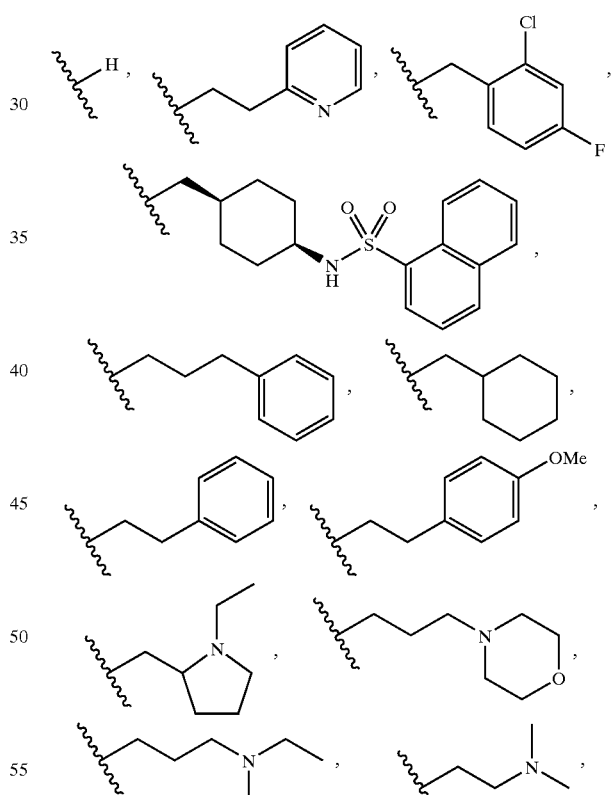
wherein $R^{20}$ is selected from the following structures:
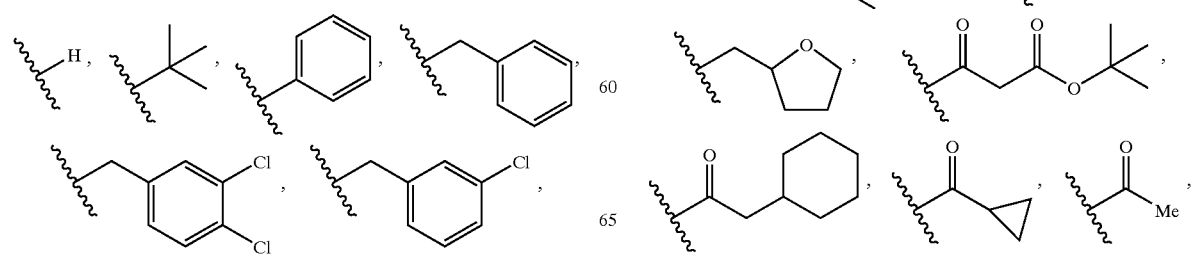

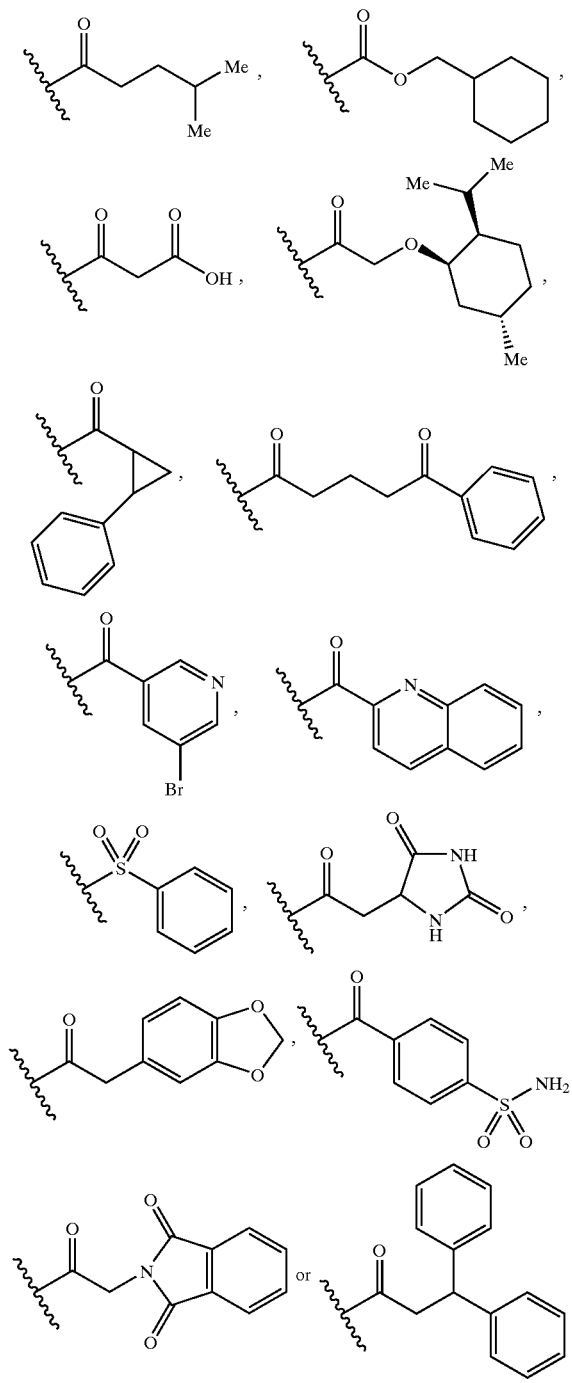
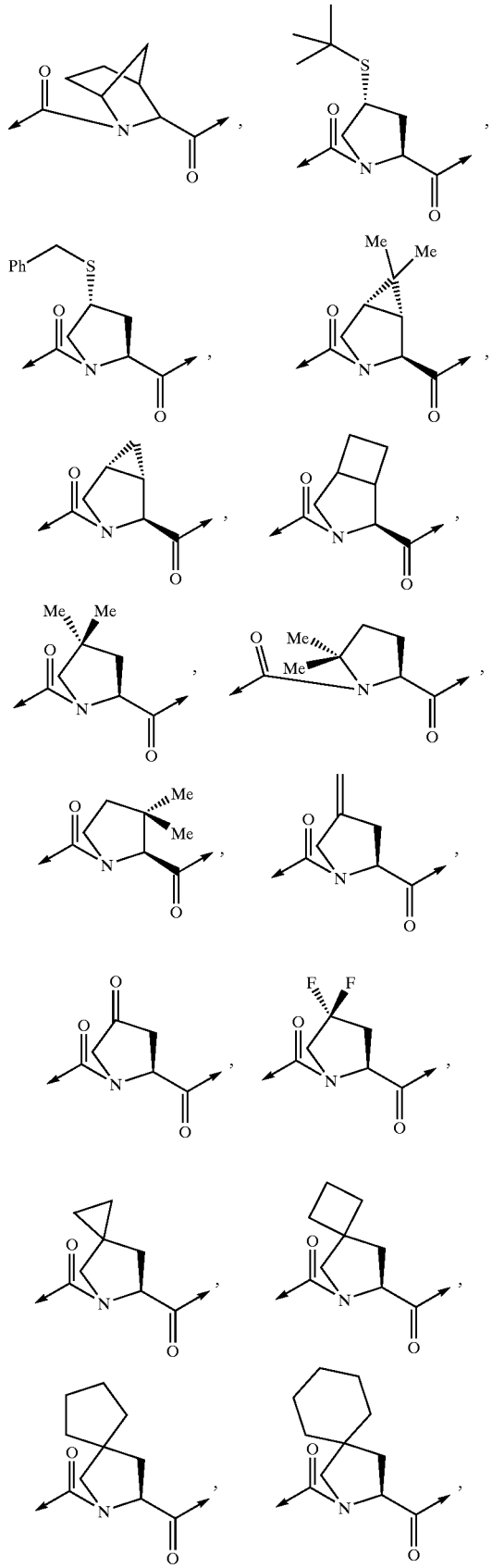
is selected from:
14. The compound of claim 10, wherein the moiety:
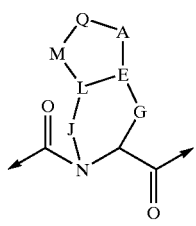
is selected from:

-continued
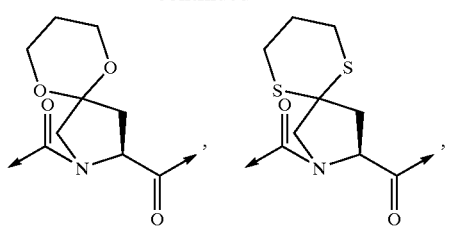
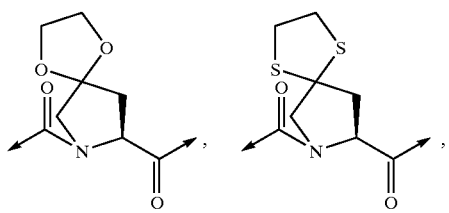
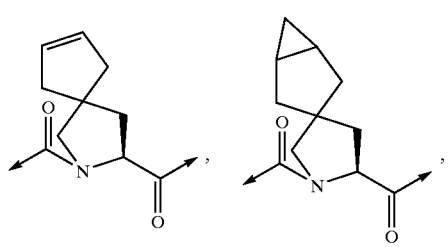
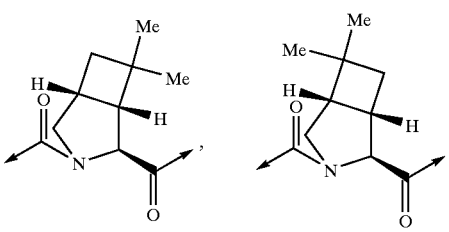
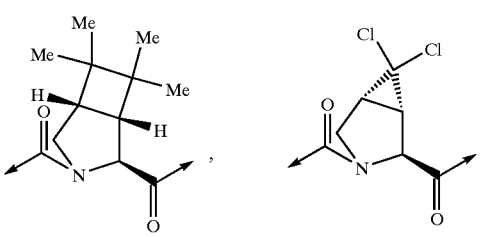
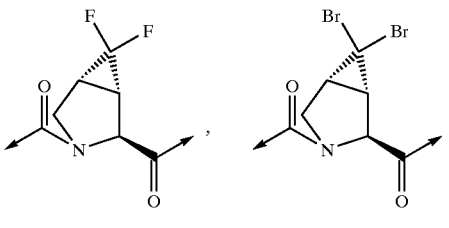
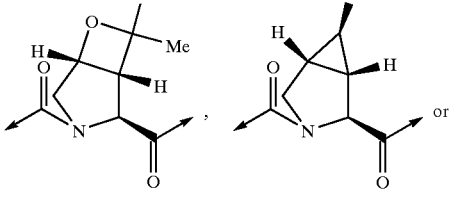
-continued
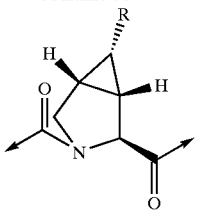
15. The compound of claim 11, wherein the moiety:
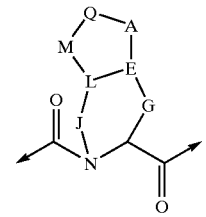
is selected from:
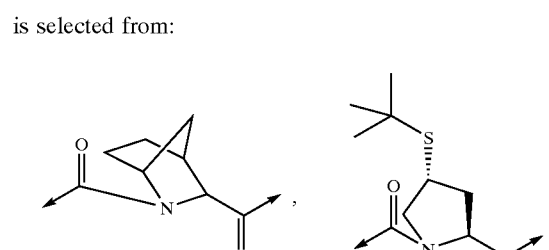
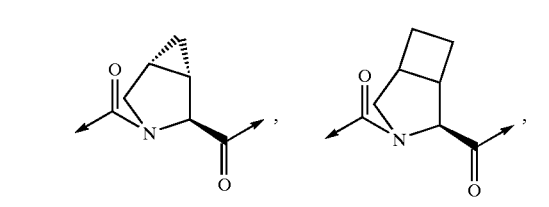
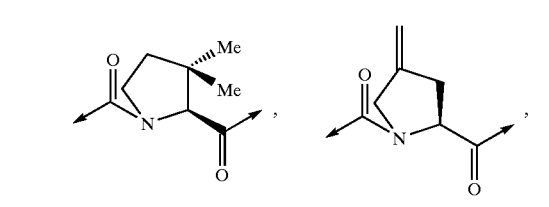

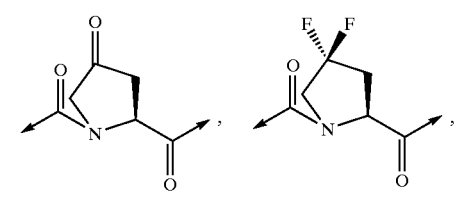
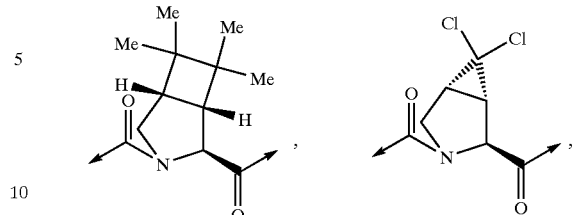
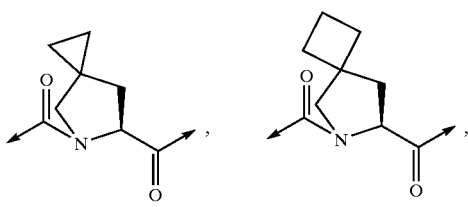
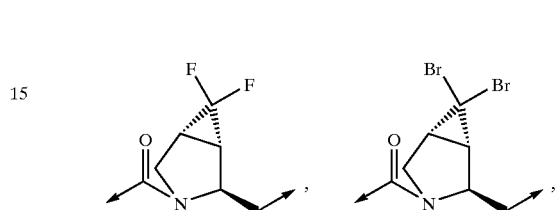
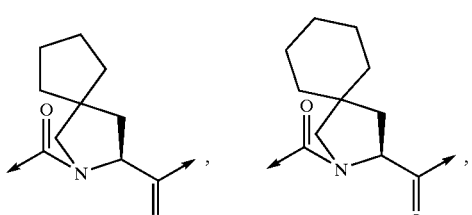
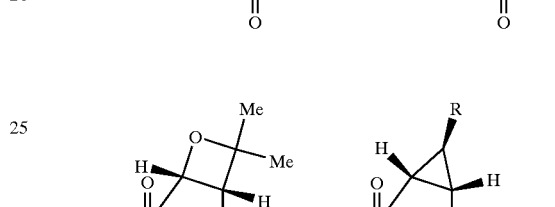
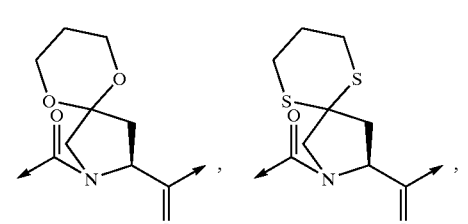
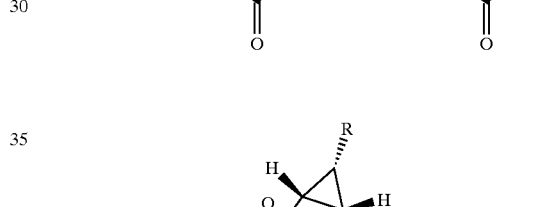
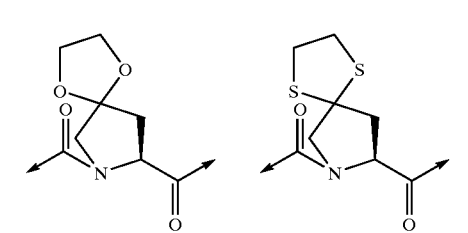
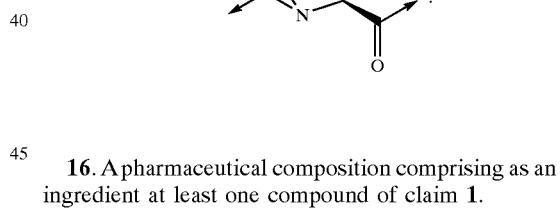

16. A pharmaceutical composition comprising as an active ingredient at least one compound of claim 1.

17. The pharmaceutical composition of claim 16 additionally comprising at least one pharmaceutically acceptable carrier.

18. The pharmaceutical composition of claim 17, additionally containing ant least one antiviral agent.

19. The pharmaceutical composition of claim 18, still additionally containing an interferon or pegylated interferon.

20. The pharmaceutical composition of claim 19, wherein said at least one antiviral agent is ribavirin and said interferon is α-interferon or pegylated interferon.

21. The compound of claim 1, wherein said compound is selected from the group consisting of:

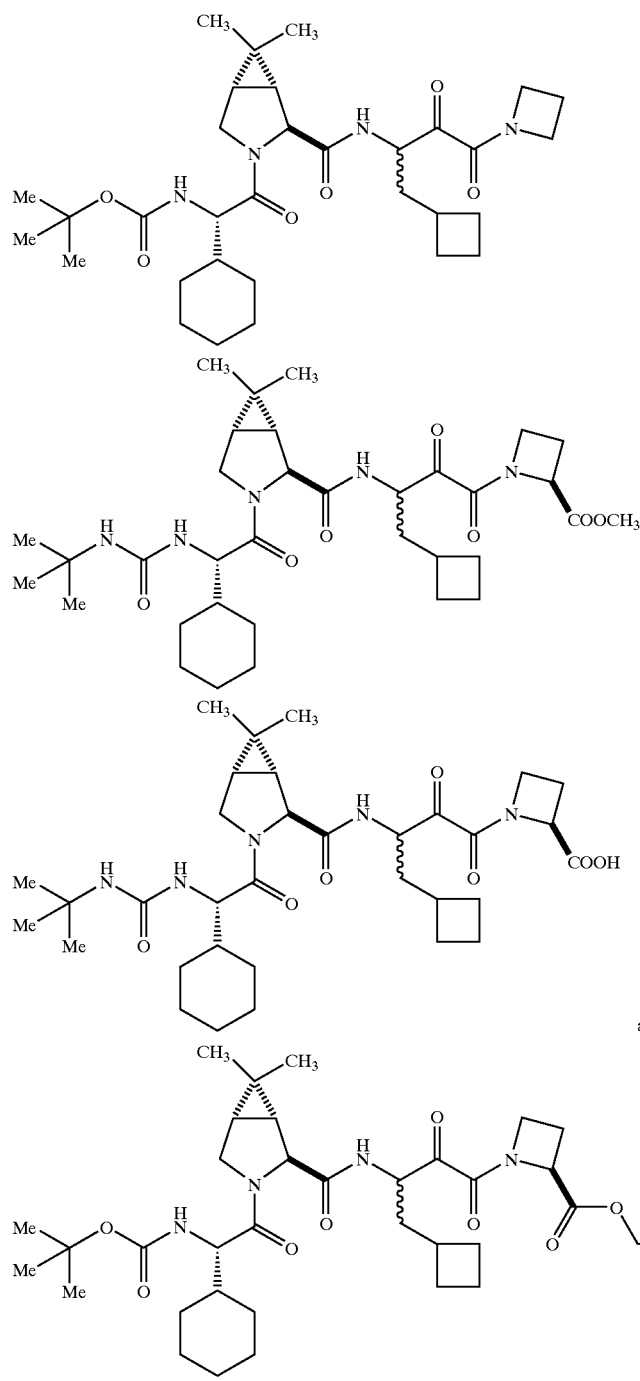

or a pharmaceutically acceptable salt or solvate of said compound.

22. A pharmaceutical composition comprising therapeutically effective amount of one or more compounds in claim 21 and a pharmaceutically acceptable carrier.

23. The pharmaceutical composition of claim 22, additionally containing at least one antiviral agent.

24. The pharmaceutical composition of claim 22, still additionally containing an interferon or a pegylated interferon.

25. The pharmaceutical composition of claim 23, wherein said antiviral agent is ribavirin and said interferon is α-interferon or pegylated interferon.

* * * * *

UNITED STATES PATENT AND TRADEMARK OFFICE
CERTIFICATE OF CORRECTION

PATENT NO.    : 6,894,072 B2
DATED         : May 17, 2005
INVENTOR(S)   : Arasappan, Ashok Page 1 of 1

It is certified that error appears in the above-identified patent and that said Letters Patent is hereby corrected as shown below:

Column 51,
Line 17, please correct to: -- selected from C=O or C=S; --.

Column 57,
Lines 35-40, the structure 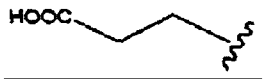 should be corrected to: 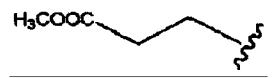

Column 69,
Lines 10-20, the structure 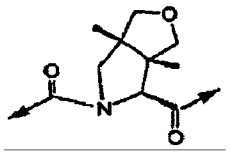 should be corrected to: 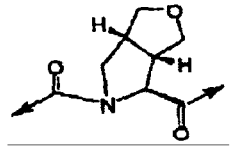

Column 70,
Lines 5-10, the second structuure  should be corrected to: 

Column 73,
Lines 45-50, the structure 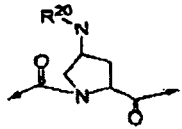 should be changed to: 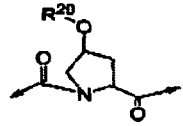

Signed and Sealed this

Twenty-third Day of August, 2005

JON W. DUDAS
*Director of the United States Patent and Trademark Office*